US012673012B2

(12) United States Patent
Lin et al.

(10) Patent No.: US 12,673,012 B2
(45) Date of Patent: Jul. 7, 2026

(54) STABLE FOAMED CLEANSING COMPOSITION AND METHODS OF USE

(71) Applicant: L'OREAL, Paris (FR)

(72) Inventors: Hungta Lin, Teaneck, NJ (US); Ritesh Kumar Sinha, Linden, NJ (US); Trung Vu, Clark, NJ (US); Mariko Hasebe, New York, NY (US); Hy Si Bui, Piscataway, NJ (US)

(73) Assignee: L'OREAL, Paris (FR)

( * ) Notice: Subject to any disclaimer, the term of this patent is extended or adjusted under 35 U.S.C. 154(b) by 294 days.

(21) Appl. No.: 18/592,000

(22) Filed: Feb. 29, 2024

(65) Prior Publication Data

US 2025/0275894 A1 Sep. 4, 2025

(51) Int. Cl.

| | |
|---|---|
| ***A61Q 19/00*** | (2006.01) |
| ***A61K 8/04*** | (2006.01) |
| ***A61K 8/19*** | (2006.01) |
| ***A61K 8/34*** | (2006.01) |
| ***A61K 8/37*** | (2006.01) |
| ***A61K 8/44*** | (2006.01) |

(Continued)

(52) U.S. Cl.

CPC ................ *A61K 8/046* (2013.01); *A61K 8/19* (2013.01); *A61K 8/345* (2013.01); *A61K 8/37* (2013.01); *A61K 8/442* (2013.01); *A61K 8/58* (2013.01); *A61Q 5/02* (2013.01); *A61Q 19/10* (2013.01)

(58) Field of Classification Search

CPC .......... A61K 8/046; A61K 8/19; A61K 8/345; A61K 8/37; A61K 8/442; A61K 8/58; A61K 8/20; A61K 2800/596; A61K 8/0295; A61K 8/41; A61K 8/44; A61K 8/463; A61K 8/466; A61K 8/60; A61Q 5/02; A61Q 19/10

USPC .................................................. 510/119, 135

See application file for complete search history.

(56) References Cited

U.S. PATENT DOCUMENTS

| | | | |
|---|---|---|---|
| 5,888,489 | A | 3/1999 | von Mallek |
| 7,744,655 | B2 | 6/2010 | De Boni et al. |

(Continued)

FOREIGN PATENT DOCUMENTS

| | | | | |
|---|---|---|---|---|
| CN | 113396206 A | * | 9/2021 | ............... C11D 3/33 |
| CN | 110585090 B | | 6/2022 | |
| EP | 2811972 B1 | | 2/2016 | |

OTHER PUBLICATIONS

International Search Report and Written Opinion issued on May 26, 2025 for corresponding PCT Application No. PCT/US2025/014732.

*Primary Examiner* — Eisa B Elhilo

(74) *Attorney, Agent, or Firm* — POLSINELLI PC

(57) ABSTRACT

The present disclosure describes stable foamed cleansing compositions. The compositions include: (a) about 8 wt. % to about 40 wt. % of one or more acyl glycinate surfactants, salts thereof, or combinations thereof; (b) one or more magnesium salts providing divalent cations having a charge density of about 40 to about 200 C/mm$^3$ and a water solubility of at least 400 g/L; (c) one or more nonionic emulsifiers having a Hydrophile-Lipophile Balance (HLB) of about 6 or less; (d) one or more water soluble solvents; and (e) water. The compositions typically have a lamellar liquid crystal structure and a specific gravity of about 0.6 to about 0.8 g/mL at 25° C. The stable foamed cleansing compositions are particularly useful in methods for cleansing the body, including the skin and hair.

20 Claims, 1 Drawing Sheet

Stable Foamed Cleansing Composition after 2 Months (4 Weeks) Storage at 25°C
Specific Gravity at 2 Months (4 Weeks) = 0.81 g/mL

(51) Int. Cl.

| | |
|---|---|
| ***A61K 8/58*** | (2006.01) |
| ***A61Q 5/02*** | (2006.01) |
| ***A61Q 19/10*** | (2006.01) |

(56) References Cited

U.S. PATENT DOCUMENTS

| | | | |
|---|---|---|---|
| 7,947,260 | B2 | 5/2011 | Tobita |
| 8,450,260 | B2 | 5/2013 | Crawford et al. |
| 9,248,083 | B2 | 2/2016 | Aires et al. |
| 9,408,785 | B2 | 8/2016 | Pistorio et al. |
| 10,328,009 | B1 | 6/2019 | Elsen-Wahrer et al. |
| 10,548,832 | B2 | 2/2020 | Thomas et al. |
| 10,561,592 | B2 | 2/2020 | Darras et al. |
| 10,912,728 | B2 | 2/2021 | D'Arras et al. |
| 11,458,084 | B2 | 10/2022 | Park et al. |
| 2002/0176843 | A1 | 11/2002 | Creton |
| 2002/0182238 | A1 | 12/2002 | Creton |
| 2005/0158269 | A1 | 7/2005 | Simonet |
| 2005/0222001 | A1 | 10/2005 | Baumeister et al. |
| 2007/0128256 | A1 | 6/2007 | Aubrun-Sonneville |
| 2008/0008672 | A1* | 1/2008 | Tobita ...................... C11D 3/33 510/158 |
| 2008/0014162 | A1 | 1/2008 | Willemin et al. |
| 2011/0171151 | A1 | 7/2011 | Arnaud et al. |
| 2013/0011360 | A1 | 1/2013 | Viravau et al. |
| 2013/0210696 | A1 | 8/2013 | Vethamuthu et al. |
| 2015/0297481 | A1 | 10/2015 | Wahler et al. |
| 2015/0359722 | A1 | 12/2015 | Thomas et al. |
| 2017/0189286 | A1 | 7/2017 | George et al. |
| 2017/0326044 | A1 | 11/2017 | Springinsfeld et al. |
| 2019/0060196 | A1 | 2/2019 | Elsen et al. |
| 2019/0216692 | A1 | 7/2019 | Luan et al. |
| 2019/0290557 | A1 | 9/2019 | Shimizu et al. |
| 2020/0188282 | A1 | 6/2020 | Chodorowski-Kimmes |
| 2020/0188283 | A1 | 6/2020 | Chodorowski-Kimmes |
| 2022/0362128 | A1 | 11/2022 | Hamazaki et al. |
| 2022/0378683 | A1 | 12/2022 | Stebbins et al. |

* cited by examiner

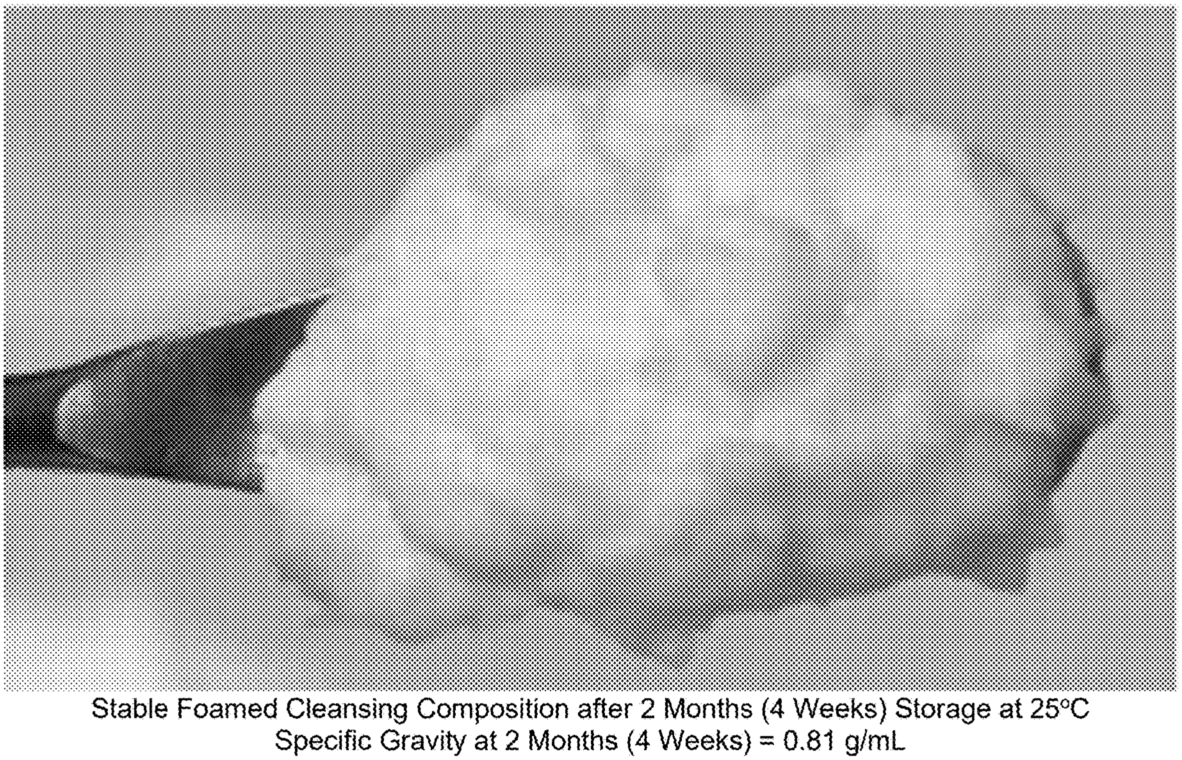
Stable Foamed Cleansing Composition after 2 Months (4 Weeks) Storage at 25°C
Specific Gravity at 2 Months (4 Weeks) = 0.81 g/mL

STABLE FOAMED CLEANSING COMPOSITION AND METHODS OF USE

FIELD OF THE DISCLOSURE

The present disclosure relates to stable foamed cleansing compositions and methods for cleansing the hair or body with the compositions.

BACKGROUND

Most "dirt" contains traces of oil and grease, which stick to the surface of the skin and hair. Rinsing with only water is not sufficient to adequately remove the oil and grease. The main functional ingredients in cleansing compositions are surfactants. Surfactants interact with water, thereby allowing it to "wet" surfaces more efficiently. The surfactant-water combination is then able to surround the specks of dirt and carry them away with rinsing. Agitation of the water solution, for example by rubbing hands together during washing or lathering shampoo into hair, also aids the process of removing dirt.

Conventional cleansing compositions such as shampoos, for example, contain surfactants in various amounts. Anionic surfactants are typically included because they provide foaming to a composition. Nonionic surfactants may also be included to provide cleansing, solubilizing, and dispersing properties but are usually less irritating than anionic surfactants. Nonionic surfactants, however, often exhibit less foaming ability and do not provide any enhancement to viscosity (e.g., often a composition is thinner and runnier with increased amounts of nonionic surfactants). In some cleansing applications, higher viscosity is desired for the product's handling or ease of application. In addition, higher viscosity personal care products are more aesthetically appealing to many consumers.

The development of cleansing compositions has been driven by a need for certain performance properties that consumers find desirable. For example, consumers seek cleansing compositions that foam and cleanse well, have a certain "thickness" (viscosity), and are mild to the skin and hair. The cleansing compositions should also rinse away from the body with ease. However, the addition of a particular component to a cleansing composition often will enhance one desired property to the detriment of another desired property. It is therefore difficult to achieve a perfect balance of desirable performance properties.

Consumers enjoy cosmetic products that provide unique sensory properties in addition to their intended cosmetic properties. Skin and hair care products are often creamy emulsions or dispersions having an aqueous phase and a hydrophobic phase. Emulsion-type or dispersion-type cosmetic products can be unsatisfactory, especially for cleansing products. They tend to be heavy and oily and often do not satisfactorily cleanse the hair or skin. Gel-type products have been developed, which typically contain various types of thickeners, especially thickening polymers. Thickening polymers are sometimes used to enhance viscosity of cleansing compositions but they can reduce the effectiveness of surfactant systems, jeopardize stability, and even fail to satisfactorily thicken as desired.

Cleansing products in the form of unstable foams, which are temporarily generated by the user immediately prior to use, are known. Unstable foamed products include aerosol products, which are foamed at the time of use by means of a propellant gas in a pressurized container. Alternatively unstable foamed cleansers can be produced by dispensing a cleansing composition from a container by means of a mechanical pump in connection with a foam head that incorporates air into the cleansing composition when dispensing the composition. These types of temporary foams break down quickly, typically within a few minutes, and require special packaging and user action to generate the foam.

Regardless of whether a cleansing composition is pre-foamed prior to use or foamed while being dispensed from a container, cleansing compositions are known to automatically generate foam and lather during use. Upon mixing with extraneous water during the cleansing process, cleansing compositions will automatically generate foam and lather. This is due to inclusion of cleansing surfactants, especially anionic surfactants. Anionic surfactants have a fatty group and a negatively charged head group that allows them to easily interact with water molecules and reduce surface between the water and fatty substances, which assists with removal of debris, makeup, and oils from the skin or hair. Popular anionic surfactants used in cleansing compositions include alkyl sulphates, in particular, sodium lauryl sulphate (SLS) and sodium laureth sulphate (SLES). Although they provide good cleansing activity and contribute to the generation of foam and lather during use, they cause irritation to the skin of certain sensitive individuals and have the potential to cause dryness.

Unlike the cleansing products discussed above, the cleansing compositions of the instant case do not require an aerosol system or other special packaging or equipment for generating a foam prior to use. The cleansing compositions are already foamed. The foamed structure is stably retained from the time of manufacture until used by consumers, which can be months or even years. Although the cleansing compositions can certainly produce additional foam and lather during use, this is not necessary. It is not necessary to include surfactants that cause cleansing compositions to foam and lather during use because the compositions are already foamed. This allows for use of milder and gentler anionic surfactants, without concern for their foaming ability during use.

SUMMARY OF THE DISCLOSURE

The present disclosure is drawn to stable foamed cleansing compositions containing a unique combination of acyl glycinate surfactants, magnesium salts, and nonionic emulsifiers having a low Hydrophile-Lipophile Balance (HLB). The inventors discovered that acyl glycinate surfactants interact with magnesium salts to enhance and stabilize foamed cleansing compositions. Acyl glycinate surfactants are anionic surfactants that provide cleansing properties to the compositions but also interact with the magnesium salts. The compositions are foamed, have a unique microstructure, and a light, pleasant texture that consumers find appealing. The compositions are not oily or sticky. Further, the foamed cleansing compositions are very effective for cleansing skin and hair, without irritation and dryness. To the contrary, the cleansing compositions surprisingly hydrate and refresh the skin despite their robust cleansing effectiveness.

The stable foamed cleansing compositions typically include:

(a) one or more acyl glycinate surfactants, salts thereof, or combinations thereof;

(b) one or more magnesium salts providing divalent cations having a charge density of about 40 to about 200 C/$mm^3$ and a water solubility of at least 400 g/L;

(c) one or more nonionic emulsifiers having a Hydrophile-Lipophile Balance (HLB) of about 6 or less;

(d) one or more water soluble solvents; and (e) water.

The compositions typically have a lamellar liquid crystal structure. Air or gas can be incorporated into the composition to foam the composition. Useful gases include inert gases, for example, nitrogen, carbon dioxide, nitrogen oxides, noble gases or mixtures of these gases. In some instances, inert oxygen-free gases, such as nitrogen or carbon dioxide, are uses, especially when the cleansing composition includes one or more oxygen sensitive ingredients. The stable foamed cleansing compositions are unique in that special "foaming" equipment is required to generate the foamed product, although special foaming equipment can certainly be used. For example, the foamed cleansing compositions can be "foamed" using a mixer, whipper, a whisk, a blender, and the like.

The foamed cleansing compositions typically have a specific gravity of about 0.6 to about 0.8 g/ml at 25° C., preferably about 0.65 to about 0.8 g/ml at 25° C., more preferably about 0.7 to about 0.8 g/ml at 25° C. Surprisingly, the foamed cleansing compositions remain stably foamed, for example, the initial specific gravity of the foamed composition is essentially unchanged over time, for example, when stored at 25° C. for 2 months.

Nonlimiting examples of acyl glycinate surfactants include sodium cocoyl glycinate, sodium lauroyl glycinate, sodium myristoyl glycinate, potassium lauroyl glycinate, potassium cocoyl glycinate, or mixtures thereof. Sodium cocoyl glycinate is particularly useful.

Nonlimiting examples of magnesium salts providing divalent cations having a charge density of about 40 to about 200 C/mm$^3$ and a water solubility of at least 400 g/L include magnesium chloride, magnesium sulfate, magnesium thiosulfate, magnesium pyrrolidone carboxylate (magnesium pidolate), magnesium gluconate, or mixtures thereof.

The term "hydrophilic-lipophilic balance ("HLB") of a surfactant is a measure of its degree of hydrophilicity or lipophilicity, determined by calculating percentages of molecular weights for the hydrophilic and lipophilic portions of the surfactant molecule. Nonlimiting examples of nonionic emulsifiers having a Hydrophile-Lipophile Balance (HLB) of about 6 or less include sorbitan esters, glyceryl esters, glycol esters, polyglyceryl esters, glycol esters, sucrose esters, methyl glucose esters, ethoxylated methyl glucose esters, or mixtures thereof. In some instances, glycol and/or glyceryl esters are particularly useful. Nonlimiting examples include glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, or mixtures thereof.

The foamed cleansing compositions typically include substantial amounts of one or more water-soluble solvents (or "water-soluble organic solvents"). Nonlimiting examples of water-soluble solvents include glycerin, $C_2$-$C_6$ mono-alcohols, polyols (polyhydric alcohols), glycols, and a combination thereof. In certain instances, water soluble solvents selected from glycerin, glycols, or mixtures thereof, are particularly useful. Nonlimiting examples of glycols include ethylene glycol, propylene glycol, butylene glycol, hexylene glycol, pentylene glycol, diethylene glycol, dipropylene glycol, caprylyl glycol, or mixtures thereof.

The foamed cleansing compositions typically include water, for example, in amounts from about 5 wt. % to about 60 wt. %, based on the total weight of the unfoamed cleansing composition. Regardless, the amount of water may be in a similar amount as the amount of the one or more water soluble solvents. For example, the weight ratio of the one or more water soluble solvents to the water may be from about 0.5:1 to about 8:1. Further, the weight ratio of the one or more water soluble solvents to the water may be from about 1:1 to about 5:1.

The stable foamed cleansing composition may optionally include one or more additional salts, other then the magnesium salts providing divalent cations having a charge density of about 40 to about 200 C/mm$^3$ and a water solubility of at least 400 g/L. For example, in various embodiments, the stable cleansing composition includes one or more salts providing monovalent cations. Nonlimiting examples include sodium chloride, potassium chloride, sodium sulphate, potassium sulphate, ammonium chloride, monoethanolammonium chloride, or mixtures thereof. Particularly preferred salts providing monovalent cations include sodium chloride, potassium chloride, or a mixture thereof.

The stable foamed cleansing compositions optionally include one or more thickening agents. Unique features of the stable cleansing compositions include their stability, viscosity, and pleasant texture. Surprisingly, these features are obtained without requiring a thickening agent. Thickening agents are often required to ensure sufficient viscosity, stability, etc. Although thickening agents are not required for the stable foamed cleansing compositions of the instant, they may optionally be included, and in some instanced, preferably included in the stable foamed cleansing compositions. On the other hand, the stable foamed cleansing compositions may be free or essentially free of one or more thickening agents. Nonlimiting examples of thickening agents include thickening polymers, such as anionic, cationic, amphoteric, and nonionic thickening polymers, and non-polymeric thickening agents such as clays (e.g., smectite, hectorite, and montmorillonite, etc.).

In various embodiments, the stable foamed cleansing compositions include one or more miscellaneous ingredients. Nonlimiting examples, include preservatives, fragrances, pH adjusters, salts, chelating agents, skin active ingredients, buffers, antioxidants, flavonoids, de-pigmenting agents, anti-wrinkle agents, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

The instant disclosure is also drawn to a cleansing products comprising the stable cleansing compositions. Such products can have a container or packaging to house or hold the stable foamed cleansing composition. Nonlimiting examples of useful containers or packaging include bottles, tubes, jars, cans, bags, boxes, and the like. The stable foamed cleansing compositions are usually foamed prior to incorporation into a container or packaging and remain stably foamed within the container or packaging. Therefore, the container or packing does not require a mechanism for generating foam, for example, a foam actuator or foaming spout. Similarly, the cleansing product is typically not an aerosol-type product, i.e., there is no need for a propellant and mechanism for foaming. It is conceivable that a pressurized or aerosol-type container be used for housing the stable foamed cleansing composition, but it would not necessarily be needed for foaming the composition but could be used to expel the already foamed cleansing composition from a container in a convenient manner.

The stable foamed cleansing compositions exhibit excellent cleansing ability, stability, and hydrating properties. Thus, the instant disclosure relates to methods of cleansing a substrate, for example, skin, hair, or a combination thereof. The methods entail applying an effective amount of a stable foamed cleansing composition to the substrate (e.g., hair, skin, or combination thereof) and rinsing the compositions from the substrate. Typically, the stable foamed cleansing composition is massaged or scrubbed over/throughout the substrate, optionally with extraneous water, to dislodge, absorb, and remove material from the substrate. The stable foamed cleansing compositions not only cleanse but can hydrate and refresh hair and/or skin. Therefore, the instant disclosure also encompasses methods for hydrating and/or refreshing the hair and/or skin.

BRIEF DESCRIPTION OF THE DRAWING

Implementation of the present technology is described, by way of example only, with reference to the attached FIGURE, wherein:

The FIGURE shows a picture of a stable foamed cleansing composition according to the instant disclosure after storage for 2 month (4 weeks) at 25° C. having a specific gravity of 0.81 g/mL.

DETAILED DESCRIPTION OF THE DISCLOSURE

The instant disclosure is drawn to stable foamed cleansing compositions. The compositions are particularly useful for cleansing the body including skin and hair, hydrating the skin and/or the hair, and refreshing the natural and radiant look of skin and/or hair. As the name suggests, the "stable foamed cleansing compositions" are both "stable" and "foamed." They include a unique combination of one or more acyl glycinate surfactants, one or more magnesium salts, and one or more nonionic emulsifiers having a Hydrophile-Lipophile Balance (HLB) of about 6 or lower. In addition, the stable foamed cleansing composition have an unusual and unique lamellar liquid crystal structure. The inventors found that acyl glycinate surfactants interact with magnesium salts to influence rheology and to stabilized foamed compositions containing them. The foamed cleansing compositions are particularly effective for cleansing skin and hair, without irritation and dryness. To the contrary, the cleansing compositions surprisingly hydrate and refresh the skin despite their robust cleansing power.

The stable foamed cleansing compositions include:

(a) about 8 wt. % to about 40 wt. % of one or more acyl glycinate surfactants, salts thereof, or combinations thereof;

(b) about 0.5 to about 2 wt. % of one or more magnesium salts providing divalent cations having a charge density of about 40 to about 200 C/mm$^3$ and a water solubility of at least 400 g/L;

(c) about 3 wt. % to about 7 wt. % of one or more nonionic emulsifiers having a Hydrophile-Lipophile Balance (HLB) of about 6 or less;

(d) about 25 to about 65 wt. % of one or more water soluble solvents; and (e) about 10 to about 55 wt. % of water;

wherein the composition has a lamellar liquid crystal structure, the composition has been foamed by incorporation of an air or gas throughout the composition;

the composition has a specific gravity of about 0.6 to about 0.8 g/ml at 25° C., and all percentages by weight are based on a total weight of unfoamed composition.

The weight percentages of the various ingredients can be referred to relative to the total weight of the unfoamed composition or relative to the total weight of the foamed composition. Incorporating air or gas into the composition (i.e., foaming the composition) does not change or does not appreciably change the weight percentages of the ingredients or the total weight of the composition. Throughout the disclosure reference is made to weight percentages based on the total weight of the unfoamed composition. In each instance, the weight percentages may be considered the same weight percentages based on the total weight of the foamed composition.

The term "stable foam" can be substituted with the term "permanent foam" and refers to the product/composition mass, which is characterized in that a gaseous substance in the form of gas bubbles is uniformly distributed throughout the product/composition and remains homogeneously distributed over a time interval of at least one week, preferably at least one month, especially preferably at least six months during storage at room temperature (25° C.). Typically, the foam degree amounts to at least 10%, preferably at least 20% of the foamed product/composition. Gas bubbles of a size, for example, between about 0.0001 and about 10 mm, especially preferably between about 0.01 and about 1 mm, are contained in the foamed product/composition mass. The average diameter of the gas bubbles may be, for example, from about 0.1 to about 0.8 mm, especially preferably from about 0.2 to about 0.4 mm.

the term "about" means within +/−5% of the indicated number. For example, an amount of "about 1 wt." can include an amount as low as 0.95 wt. % or as high as 1.05. Similarly, an amount of "about 50" can include an amount as low as 47.5 wt. % and as high as 52.5. The specific gravity for the stable cleansing compositions is described below (and throughout the specification) as having a maximum about "about 0.8 g/ml at 25° C." The data in the examples show that compositions having a specific gravity of 0.81 g/ml (inventive composition E) and 0.83 (inventive composition D) were stable. The specific gravity of 0.81 and 0.83 are encompassed by the phrase "about 0.8 g/ml." The amount of "about 0.8" ranges from 0.76 to 0.84 (amounts +/−5% of 0.8). Accordingly, the ranges described throughout the disclosure, for example, a range for a specific gravity being "about 0.6 to about 0.8 g/ml" may be written by omitting the term "about" as "0.57 to 0.84 g/ml." This range accounts for the minimum amounts of "about 0.6" and the maximum amount for "about 0.8." The other ranges should be interpreted similarly. Specifically, the specific gravity can be written as 0.57 to 0.84 g/ml at 25° C., preferably 0.62 to 0.84 g/ml at 25° C., more preferably 0.67 to 0.84 g/ml at 25° C. In a preferred embodiment, the specific gravity is from 0.7 to 0.83 gm/ml at 25° C.

The inventors discovered that when the cleansing compositions are foamed such that they have a specific gravity of about 0.6 to about 0.8 g/ml at 25° C., preferably about 0.65 to about 0.8 g/ml at 25° C., more preferably about 0.7 to about 0.8 g/ml at 25° C., they remain particularly stable. The term "stable" as used throughout the instant disclosure, means that the foamed cleansing compositions substantially retains its original volume, i.e., the volume of the foamed cleansing composition after it is immediately prepared does not substantially change over time. For example, the stable foamed cleansing composition may have a specific gravity of about 0.6 to about 0.8 g/ml at 25° C., preferably about 0.65 to about 0.8 g/ml at 25° C., more preferably about 0.7 to about 0.8 g/ml at 25° C. immediately upon manufacture and also have a specific gravity of about 0.6 to about 0.8 g/ml at 25° C., preferably about 0.65 to about 0.8 g/ml at 25° C., more preferably about 0.7 to about 0.8 g/ml at 25° C., after storage at 25° C. for at least 2 weeks, preferably after at least 4 weeks, more preferably after at least 2 months (or 8 weeks), even more preferably after at least 6 months (26 weeks). Furthermore, in various embodiments, the specific gravity of the stable foamed cleansing composition immediately after manufacture does not change by more than 25%, preferably not more than 20%, more preferably not more than 15 wt. %, even more preferably not more than 10%, and ideally not more than 5% after storage at 25° C. for at least 2 weeks, preferably at least 4 weeks, more preferably at least 2 months (or 8 weeks), even more preferably after at least 6 months (26 weeks).

The stable foamed cleansing compositions are unique in that special “foaming” equipment is required to generate the foamed product, although special foaming equipment can certainly be used. For example, the stable foamed cleansing compositions can be “foamed” using a standard mixer, whipper, whisk, blender, and the like. The forcing in or foaming with air and/or inert gas can occur by means of a suitable apparatus specific for that purpose, e.g. by means of a rapidly running stirring device or stirrer, so that gas from the surrounding atmosphere (preferably air) is introduced into the mass. The foaming can also occur when the unfoamed composition is conducted through a mixer, which has a mixing head and a feed device with respective connectors for supplying it and the gas simultaneously to the mixing head. The composition can be acted on with a gas, preferably air, $CO_2$ or nitrogen, in a gas mixing unit (e.g. as Euromix or a dynamic foam generator top mix from a Hansa Industry mixer or with an Ultra Turax laboratory mixer).

The use of nitrogen is especially preferred, for example, when the stable foamed cleansing composition includes oxygen sensitive ingredients. For example, various vitamins, antioxidants, skin active agents, etc., which may be included in the stable foamed cleansing compositions may be sensitive to oxygen (i.e., the oxygen might oxidize, discolor, inactivate, or destabilize the ingredients or even the compositions as a whole). The forcing in of air and/or inert gas is preferably in a range between 20 and 200%. The forcing in or action of air and/or inert gas influences the structure and consistency and can be adjusted as desired.

The stable foamed cleansing compositions typically have an opaque or white, and creamy appearance.

Due to their robust cleansing and hydrating properties of the stable foamed cleansing compositions, they are particularly useful as a skin cleanser, a hair cleanser (shampoo), a body wash, a cleansing and hydrating cleanser, an all-in-one conditioning and shampooing composition, or a general-purpose cleanser. The cleansing compositions are particularly useful in methods for cleansing the body, including the skin and hair. Such methods include applying the cleansing composition to the body or area to be cleansed (skin or hair), massaging the cleansing composition over the area to be cleansed (or throughout the hair), and rinsing the cleansing composition from the body.

(a) Acyl Glycinate Surfactants

Acyl glycinate surfactants include those of formula (X):

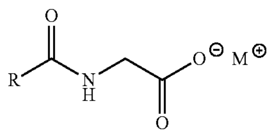

(X)

wherein R is an alkyl chain of 8 to 16 carbon atoms and M is a cation. Cations include alkali metal ions such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, potassium cocoyl glycinate, or mixtures thereof. In a preferred embodiments, the one or more acyl isethionate surfactants is sodium cocoyl glycinate.

In various embodiments, the only anionic surfactants in the stable foamed cleansing composition are the one or more acyl glycinate surfactants. Thus, the stable foamed cleansing composition may be free or substantially free from anionic surfactants other than the one or more acyl isethionate surfactants.

In certain embodiments, the stable foamed cleansing composition includes one or more acyl isethionate surfactants selected from sodium cocoyl glycinate, potassium cocoyl glycinate, or a mixture thereof. In further embodiments, the stable foamed cleansing composition includes sodium cocoyl glycinate and is preferably free or essentially free from anionic surfactants other than acyl glycinate surfactants, even more preferably, wherein the only anionic surfactant in the stable foamed cleansing composition is the sodium cocoyl glycinate.

The stable foamed cleansing compositions typically include from about 5 to about 45 wt. % of the one or more acyl glycinate surfactants, based on a total weight of the unfoamed cleansing composition. In further embodiments, the stable foamed cleansing compositions include from about 8 to about 45 wt. %, about 10 to about 45 wt. %, about 12 to about 45 wt. %, about 5 to about 40 wt. %, about 8 to about 40 wt. %, about 10 to about 40 wt. %, about 12 to about 40 wt. %, about 5 to about 36 wt. %, about 8 to about 36 wt. %, about 10 to about 36 wt. %, or about 12 to about 36 wt. %, based on a total weight of the unfoamed cleansing composition. In yet another embodiments, the stable foamed cleansing composition includes from about 8 to about 25 wt. %, about 10 to about 25 wt. %, about 12 to about 25 wt. %, about 8 to about 20 wt. %, about 10 to about 20 wt. %, about 12 to about 20 wt. %, about 8 to about 18 wt. %, about 10 to about 18 wt. %, or about 12 to about 18 wt. % of the one or more acyl glycinate surfactants, based on a total weight of the unfoamed cleansing composition.

In various embodiments, the stable foamed cleansing compositions includes the one or more acyl glycinate surfactants (for example, as discussed above) and optionally further includes one or more additional anionic surfactants, other than the one or more acyl glycinate surfactants. Nonlimiting examples of anionic surfactants other than acyl glycinate surfactants include sulfate-based surfactants, acyl isethionate surfactants, acyl amino acid surfactants other than the acyl glycinate surfactants (such as acyl taurate surfactants, acyl glutamate surfactants, and acyl sarcosinate surfactants), alkyl sulfonates, alkyl sulfosuccinates, alkyl sulfoacetates, alkoxylated monoacids, salts thereof, and mixtures thereof. Note that acyl glycinate surfactants are a type of acyl amino acid surfactant.

In a preferred embodiment, when the stable foamed cleansing composition includes one or more additional anionic surfactants in addition to the one or more acyl isethionate surfactants, the one or more additional anionic surfactants are preferably not sulfate-based surfactants, for example, sodium lauryl sulfate (SLS), sodium dodecyl sulfate (SDS), or a mixture thereof. The stable foamed cleansing compositions may be free or essentially free from sulfate-based surfactants, for example, free or essentially free from sodium lauryl sulfate (SLS), sodium dodecyl sulfate (SDS), or a mixture thereof.

In various embodiments, when the stable foamed cleansing composition includes one or more additional anionic surfactants in addition to the one or more acyl isethionate surfactants, the total amount of the one or more acyl isethionate surfactants is greater than the total combined amount of all additional anionic surfactants in the stable foamed cleansing composition. For example, the total weight percent of the one or more acyl glycinate surfactants in the stable foamed cleansing composition may be at least 2-fold higher than the total combined weight percent of all additional anionic surfactants in the stable foamed cleansing composition. Preferably, the total weight percent of the one or more acyl glycinate surfactants in the stable foamed cleansing composition is at least 3-fold higher, at least 4-fold higher, at least 5-fold higher, at least 8-fold higher, or at least 10-fold higher than the total combined weight percent of all additional anionic surfactants in the stable foamed cleansing composition. Along these lines the weight ratio of the total amount of the one or more acyl glycinate surfactants to the total combined amount of all additional anionic surfactants may be from about 2:1 to about 50:1, about 2:1 to about 40:1, about 2:1 to about 25:1, about 2:1 to about 20:1, about 2:1 to about 15:1, about 2:1 to about 10:1, about 2:1 to about 8:1, about 3:1 to about 50:1, about 3:1 to about 40:1, about 3:1 to about 25:1, about 3:1 to about 20:1, about 3:1 to about 15:1, about 3:1 to about 10:1, about 3:1 to about 8:1, about 5:1 to about 50:1, about 5:1 to about 40:1, about 5:1 to about 25:1, about 5:1 to about 20:1, about 5:1 to about 15:1, or about 5:1 to about 10:1.

Additional Anionic Surfactants

As used herein, the term "additional anionic surfactants" is used to refer generally to anionic surfactants other than acyl glycinate surfactants. In various embodiments, additional anionic surfactants (anionic surfactants other than the one or more acyl glycinate surfactants) may be included in the stable foamed cleansing composition. In other embodiments, additional anionic surfactants (anionic surfactants other than the one or more acyl glycinate surfactants) may be excluded from the stable foamed cleansing composition. Accordingly, the stable foamed cleansing compositions, in certain embodiments, may be free or essentially free from any one or more (or all) additional anionic surfactants (anionic surfactants other than the one or more acyl glycinate surfactants), including those set forth below.

Nonlimiting examples of anionic surfactants other than acyl glycinate surfactants include sulfate-based surfactants, acyl isethionate surfactants, acyl amino acid surfactants other than the acyl glycinate surfactants (such as acyl taurate surfactants, acyl glutamate surfactants, and acyl sarcosinate surfactants), alkyl sulfonates, alkyl sulfosuccinates, alkyl sulfoacetates, alkoxylated monoacids, salts thereof, and mixtures thereof.

(i) Sulfate-Based Surfactants

Additional anionic surfactants include sulfate-based surfactants (or simply "sulfate surfactants"). Nonlimiting examples of sulfate-based surfactants include alkyl sulfates and alkyl ether sulfates. Useful alkyl sulfates include, but are not limited to, $C_{8-18}$ alky sulfates, more preferably $C_{12-18}$ alkyl sulfates, preferably in the form of a salt with a solubilizing cation such as sodium, potassium, ammonium or substituted ammonium. Nonlimiting examples include sodium lauryl sulfate (SLS), sodium dodecyl sulfate (SDS), or a combination thereof. Useful alkyl ether sulfates include, but are not limited to, those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilizing cation such as sodium, potassium, ammonium or substituted ammonium. An example is sodium lauryl ether sulfate (SLES).

If present, the stable foamed cleansing composition typically includes about 0.01 to about 5 wt. % of one or more sulfate-based surfactants. The stable foamed cleansing composition may include from about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. % of one or more sulfate-based surfactants, based on a total weight of the unfoamed cleansing composition.

(ii) Acyl Amino Acid Surfactants

Acyl amino acid surfactants include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. Common cations associated with acyl amino acid surfactants include sodium and potassium. Alternatively, the cation can be an organic salt such as triethanolamine (TEA) or a metal salt. Non-limiting examples of useful acyl amino acids include those of formula (I):

(I)

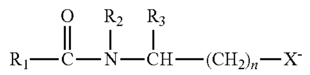

wherein R, $R^1$, $R^2$ and $R^3$ are each independently selected from H or an alkyl chain having 1-24 carbon atoms, said chain being saturated or unsaturated, linear or branched, and X is $COO^{31}$ or $SO_3^-$.

If present, the stable foamed cleansing composition typically includes about 0.01 to about 10 wt. % of one or more amino acid surfactants (other than the acyl glycinate surfactants). The stable foamed cleansing composition may include from about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 5 wt. %, about 1 to about 10 wt. %, about 1 to about 8 wt. %, about 1 to about 5 wt. %, about 1 to about 3 wt. % of one or more amino acid surfactants (other than the acyl glycinate surfactants), based on a total weight of the unfoamed cleansing composition.

In various embodiments it is preferable that the additional anionic surfactants are selected from one or more amino acid surfactants (other than the acyl glycinate surfactants). Additional amino acid surfactants may be easily formulated with the one or more acyl glycinate surfactants and are less likely to destabilize or negatively influence the desirable properties of the stable foamed cleansing composition.

Nonlimiting examples of acyl sarcosinate surfactants, acyl taurate surfactants, acyl glutamate surfactants, alkyl sulfonate surfactants, acyl isethionate surfactant, alkyl sulfosuccinate surfactants, alkyl sulfoacetate surfactants, and alkoxylated monoalcohols, are provided below.

(ii-a) Acyl Sarcosinate Surfactants

Nonlimiting examples of acyl sarcosinate surfactants include those of Formula (II) or salt thereof:

$RCON(CH_3)CH_2COOX$ (II)

wherein R is C8 to C22 alkyl or alkenyl, X is hydrogen, alkali metal, ammonium, C1 to C6 alkylamine or amino alcohol.

More specific but nonlimiting examples of acyl sarcosinate surfactants include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some instances, sodium lauroyl sarcosinate is preferred.

If present, the stable foamed cleansing composition typically includes about 0.01 to about 10 wt. % of one or more acyl sarcosinate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more acyl sarcosinate surfactants, based on a total weight of the unfoamed cleansing composition.

(ii-b) Acyl Taurate Surfactants

Non-limiting examples of acyl taurate surfactants include those of formula (III):

(III)

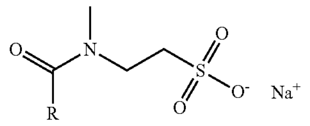

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. More specific but nonlimiting examples of acyl taurate surfactants include sodium cocoyl taurate and sodium methyl cocoyl taurate.

If present, the stable foamed cleansing composition typically includes about 0.01 to about 10 wt. % of one or more acyl taurate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more acyl taurate surfactants, based on a total weight of the unfoamed cleansing composition.

(ii-c) Acyl Glutamates

Nonlimiting examples of useful acyl glutamate surfactants include those of formula (V):

(V)

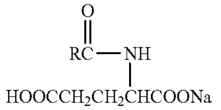

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. More specific but nonlimiting examples of acyl glutamate surfactants include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly useful.

If present, the stable foamed cleansing composition typically includes about 0.01 to about 10 wt. % of one or more acyl glutamate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more acyl glutamate surfactants, based on a total weight of the unfoamed cleansing composition.

(iii) Alkyl Sulfonate Surfactants

Nonlimiting examples of alkyl sulfonate surfactants include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (VI) is particularly useful.

(VI)

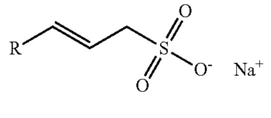

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium C14-16 olefin sulfonate.

If present, the stable foamed cleansing composition typically includes about 0.01 to about 10 wt. % of one or more alkyl sulfonate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more alkyl sulfonate surfactants, based on a total weight of the unfoamed cleansing composition.

(iv) Acyl Isethionate Surfactants

Nonlimiting examples of useful acyl isethionate surfactants include those of formula (VII) and (VIII):

(VII)

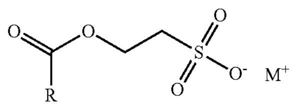

(VIII)

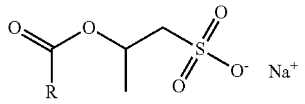

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Sodium is shown as the cation in formula (VI) but the cation for both formula (V) and formula (VI) may be an alkali metal ion such as sodium or potassium, ammonium ions, or alkanolammonium ions such as monoethanolammonium or triethanolammonium ions. More specific but nonlimiting examples of acyl isethionate surfactants include sodium isethionate, sodium cocoyl isethionate, sodium lauroyl methyl isethionate, and sodium cocoyl methyl isethionate. In some instances, sodium cocoyl methyl isethionate is a particularly useful acyl isethionate that may be included in the cleansing compositions.

If present, the stable foamed cleansing composition typically includes about 0.01 to about 10 wt. % of one or more acyl isethionate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more acyl isethionate surfactants, based on a total weight of the unfoamed cleansing composition.

(v) Alkyl Sulfosuccinate Surfactants

Non-limiting examples of useful alkyl sulfosuccinate surfactants include those of formula (IX):

(IX)

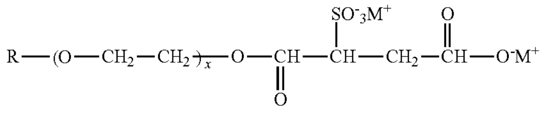

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions. More specific but nonlimiting examples of alkyl sulfosuccinate surfactants salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a combination thereof. In some instances, disodium laureth sulfosuccinate is particularly preferred.

If present, the stable foamed cleansing composition typically includes about 0.01 to about 10 wt. % of one or more alkyl sulfosuccinate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more alkyl sulfosuccinate surfactants, based on a total weight of the unfoamed cleansing composition.

(vi) Alkyl Sulfoacetate Surfactants

Nonlimiting examples of alkyl sulfoacetate surfactants includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

If present, the stable foamed cleansing composition typically includes about 0.01 to about 10 wt. % of one or more alkyl sulfoacetate surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more alkyl sulfoacetate surfactants, based on a total weight of the unfoamed cleansing composition.

(vii) Alkoxylated Monoacid Surfactants

Nonlimiting examples of alkoxylated monoacid surfactants include compounds corresponding to formula (X):

$$RO[CH_2O]_u[(CH_2)_xCH(R')(CH_2)y(CH_2)_zO]_v[CH_2CH_2O]_wCH_2COOH \quad (X)$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z>0;

Compounds corresponding to formula (VII) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (VII), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacid surfactants include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and a combination thereof.

If present, the stable foamed cleansing composition typically includes about 0.01 to about 10 wt. % of one or more alkoxylated monoacid surfactants. The stable foamed cleansing composition may include from about 0.01 to about 8 wt. %, about 0.01 to about 5 wt. %, 0.01 to about 3 wt. %, about 0.01 to about 1 wt. %, about 0.1 to about 10 wt. %, about 0.1 to about 8 wt. %, about 0.1 to about 5 wt. %, 0.1 to about 3 wt. %, about 0.1 to about 1 wt. %, about 1 to about 10 wt. %, about 1 to about 8 wt. %, or about 1 to about 5 wt. % of the one or more alkoxylated monoacid surfactants, based on a total weight of the unfoamed cleansing composition.

(c) Magnesium Salts

The inventors discovered that magnesium salts providing a divalent cation source interact synergistically with one or more acyl glycinate surfactants to provide a stabilizing effect to the foamed cleansing compositions. The magnesium salts typically have a charge density of about 40 to about 200 $C/mm^3$ and a water solubility of at least 400 g/L at 25° C. Charge density is simply the density of charge around an ion, i.e., the ratio of an ion's charge to its volume. Charge densities ($Cmm^{-3}$) are calculated according to the formula:

$$\frac{ne}{(4/3)\pi r^3}$$

where the ionic radii r are the Shannon-Prewitt values in millimeters, e is the electron charge ($1.60\times10^{-19}$ C), and n represents the ion charge.

Charge densities and methods for calculating charge densities are known in the art. See, e.g., Shannon, Revised Effective Ionic Radii and Systematic Studies of Interatomic Distances in Halides and Chalcogenides, Acta Cryst., A32: 751-767 (1976), which is incorporated herein by reference in its entirety.

The solubility of magnesium salts in water at 25° C. is also well-known, publicly available, and can be easily calculated. In certain embodiments, the magnesium salts have a solubility of at least 400 g/L. In further embodiments, the magnesium salts have a solubility of at least 450 g/L, at least 500 g/L, or at least 525 g/L.

Nonlimiting examples of magnesium salts providing a divalent cation source include magnesium chloride, magnesium sulfate, magnesium thiosulfate, magnesium pyrrolidone carboxylate (magnesium pidolate), and magnesium gluconate. In a preferred embodiment, the one or more magnesium salts are selected from magnesium chloride, magnesium gluconate, magnesium glycinate, or a mixture thereof.

The total amount of the one or more magnesium salts providing the divalent cation source is typically from about 0.5 to about 2 wt. %, based on a total weight of the unfoamed cleansing composition. The total amount of the one or more magnesium salts providing the divalent cation source may be from about 0.5 to about 1.8 wt. %, about 0.5 to about 1.6 wt. %, about 0.5 to about 1.5 wt. %, about 0.5 to about 1.3 wt. %, about 0.6 to about 2 wt. %, about 0.6 to about 1.8 wt. %, about 0.6 to about 1.5 wt. %, about 0.6 to about 1.3 wt. %, or about 0.6 to about 1.1 wt. %, based on a total weight of the unfoamed cleansing composition.

(c) Low HLB Nonionic Emulsifiers

Nonionic emulsifiers are known in the art and described in the INCI INGREDIENT DICTIONARY AND HANDBOOK (11th Edition 2006), which is incorporated herein by reference in its entirety. The hydrophilic-lipophilic balance (HLB) of a surfactant is a measure of its degree of hydrophilicity or lipophilicity, determined by calculating percentages of molecular weights for the hydrophilic and lipophilic portions of the surfactant molecule, as described by William C. Griffin, (*Calculation of HLB Values of Non-Ionic Surfactants*, J. OF THE SOC. OF COSMETIC CHEMISTS, 249-259 (1954)), which is incorporated herein by reference in its entirety.

Nonlimiting examples of nonionic emulsifiers having an HLB of about 6 or less include the following:

1. Sorbitan esters, such as, sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan trisostearate, sorbitan trioleate, sorbitan tristearate, and combinations thereof;
2. Glyceryl esters, such as glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, and combinations thereof;
3. Polyglyceryl esters, such as polyglyceryl-4 isostearate, polyglyceryl-3 oleate, polyglyceryl-2 sesquioleate, triglyceryl diisostearate, diglyceryl monooleate, tetraglyceryl monooleate, and combinations thereof;
4. Glycol esters, such as glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, and combinations thereof;
5. Sucrose esters, such as sucrose cocoate and sucrose laurate, and combinations thereof.
6. Methyl glucose esters, such as methyl glucose sesquistearate, methyl glucose dioleate, and combinations thereof;

Nonlimiting examples of nonionic emulsifier having an HLB of about 6 or less include sucrose distearate, sorbitan stearate, octyldodecyl xyloside, glyceryl stearate, and combinations thereof. Nonlimiting examples of nonionic emulsifiers having an HLB less than 5 include sorbitan sesquioleate, sorbitan trioleate, sorbitan tristearate, polyethylene sorbitan monostearate, cellulose acetate butyrate, tetradecanol, and combinations thereof.

In a preferred embodiment, the one or more nonionic emulsifiers having an HLB of about 6 or less are selected from glycol esters, glycerol esters, or a combination thereof, for example, one or more selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, diglyceryl polyacyladipate-2, glyceryl behenate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, citrate, glyceryl dioleate, glyceryl distearate, glyceryl laurate, or a combination thereof. In at least one instance the glyceryl ester comprises glyceryl stearate, bisdiglyceryl polyacyladipate, glyceryl ricinoleate, or a combination thereof.

In another preferred embodiment the one or more nonionic emulsifiers have an HLB of about 1 to about 5, such as those selected from glycol distearate, sorbitan trioleate, propylene glycol isostearate, glycol stearate, sorbitan sesquioleate, glyceryl stearate, lecithin, sorbitan oleate, sorbitan monostearate NF, sorbitan Stearate, sorbitan isostearate, steareth-2, oleth-2, or a combination thereof.

| Nonionic Emulsifiers having HLB of About 6 or Less | HLB |
|---|---|
| Ethylene glycol distearate | 1.5 |
| Sorbitan tribleate (Span 85) | 1.8 |
| Sorbitan trioleate (Arlacel 85) | 1.8 |
| Polyoxyethylene sorbitol beeswax derivative (Atlas G-1706) | 2.0 |
| Sorbitan tristearate (Span 65) | 2.1 |
| Sorbitantristearate (Arlacel 65) | 2.1 |
| Polyoxyethylene sorbitol hexastearate (Atlas G-1050) | 2.6 |
| Ethyleneglycol fatty acid ester (Emcol EO-50_ | 2.7 |
| Ethyleneglycol fatty acid ester (Emcol ES-50) | 2.7 |
| Polyoxyethylene sorbitol beeswax derivative (Atlas G-1704) | 3.0 |
| Glyceryl monooleate | 3.3 |
| Propylene glycol monostearate | 3.4 |
| Propylene glycol fatty acid ester (Emcol PO-50) | 3.4 |
| Propylene glycol fatty acid ester (Atlas G-922) | 3.4 |
| "Pure" propylene glycol fatty acid ester | 3.4 |
| Propylene glycol fatty acid ester (Atlas G-2158) | 3.4 |
| Ethylene glycol fatty acid ester (Emcol PS-50) | 3.4 |
| Ethyleneglycol fattyacid ester (Emcol EL-50) | 3.6 |
| Propylene glycol fatty acid ester (Emcol PP-50) | 3.7 |
| Sorbitan sesquioleate (Arlacel C) | 3.7 |
| Sorbitan sesquiolate (Arlacel 83) | 3.7 |
| Polyoxyethyle esorbitol 4,5 oleate (AtlasG-2859) | 3.7 |
| Glycerol monostearate (Atmul 67) | 3.8 |
| Glycerol monostearate (Atmul 84) | 3.8 |
| "Pure" hydroxylatedlanolin | 3.8 |
| Polyoxyethylene sorbitol beeswax | 4.0 |
| Propylene glycol fatty acid ester | 4.1 |
| Sorbitan monoleate (Span 80) | 4.3 |
| Propylene glycol monolaurate (Atlas G-—917) | 4.5 |
| Propylene glycol fatty acid ester (EmcolPL-50) | 4.5 |
| Sorbitan monostearate | 4.7 |
| Sorbitan Isostearate | 4.7 |
| Diethylene glycol monooleate (AtlasG-2139) | 4.7 |
| Diethyleneglycol fatty acid ester (Emcol DO-50) | 4.7 |
| Diethylene glycol monostearate (AtlasG-2146) | 4.7 |
| Diethyleneglycol fatty acid ester (Emcol DS-50) | 4.7 |
| Oolyoxyethylene sorbitol beeswax derivative (AtlasG-1702) | 5.0 |
| Diethylene glycol fatty acid ester (Emcol DP-50) | 5.1 |
| Glycerol monostearate | 5.5 |
| Glycerol monostearate | 5.5 |
| Methyl glucoside sesquistearate | 6.0 |
| Diethylene glycol monolaurate (AtlasG-2124) | 6.1 |

The total amount of the one or more nonionic emulsifiers having an HLB of about 6 or less will vary but is typically from about 1 to about 10 wt. %, based on a total weight of the unfoamed cleansing composition. Preferably, however, the stable foamed cleansing composition includes from about 3 to about 6 (or about 3 to about 7 wt. %) of the one or more nonionic emulsifiers having an HLB of about 6 or less, based on a total weight of the unfoamed cleansing composition. More preferably, however, the stable foamed cleansing composition includes from about 3 to about 6 wt. %, of the one or more nonionic emulsifiers having an HLB of about 6 or less, based on a total weight of the unfoamed cleansing composition. In various embodiments, the total amount of the one or more nonionic emulsifiers having an HLB of about 6 or less may be from about 3 to about 5 wt. %, about 3 to about 4 wt. %, about 4 to about 6 wt. %, about 4 to about 5 wt. %, or about 5 to about 6 wt. %, based on a total weight of the unfoamed cleansing composition.

(d) Water Soluble Solvent

The term "water soluble solvent" is interchangeable with the terms "water soluble organic solvent" and "water-miscible solvent" and means a compound that is liquid at 25° C. and at atmospheric pressure (760 mmHg) and has a solubility of at least 50% in water under these conditions. In some cases, the water-soluble solvent has a solubility of at least 60%, 70%, 80%, or 90%. Nonlimiting examples of water-soluble solvents include, for example, organic solvents selected from glycerin, alcohols (for example C2-8 monoalcohols), polyols (polyhydric alcohols), glycols, and mixtures thereof.

Nonlimiting examples of monoalcohols and polyols include ethyl alcohol, isopropyl alcohol, propyl alcohol, benzyl alcohol, and phenylethyl alcohol, glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Water soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a combination thereof.

Nonlimiting examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a combination thereof. Polyol compounds may also be used. Nonlimiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a combination thereof.

In a preferred embodiment, the stable foamed cleansing composition includes one or more water soluble solvents selected from glycerin and/or one or more glycols selected from ethylene glycol, propylene glycol, butylene glycol, pentylene glycol, hexylene glycol, caprylyl glycol, dipropylene glycol, or mixtures thereof. In preferred embodiment, at least one of the one or more water soluble solvents is glycerin.

The total amount of the one or more water-soluble solvents in the stable foamed cleansing composition will vary. Nonetheless, in various embodiments, the stable foamed cleansing composition includes about 5 to about 55 wt. % of one or more water soluble solvents, based on a total weight of the unfoamed cleansing composition. In further embodiments, the stable foamed hair treatment composition includes about 5 to about 50 wt. %, about 5 to about 45 wt. % about 10 to about 55 wt. %, about 10 to about 50 wt. %, about 10 to about 45 wt. %, about 15 to about 55 wt. %, about 15 to about 50 wt. %, about 15 to about 45 wt. %, about 20 to about 55 wt. %, about 20 to about 50 wt. %, about 20 to about 45 wt. %, about 25 to about 55 wt. %, about 25 to about 50 wt. %, about 25 to about 45 wt. %, about 30 to about 55 wt. %, about 30 to about 50 wt. %, or about 30 to about 45 wt. % of the one or more water soluble solvents, based on a total weight of the unfoamed cleansing composition.

In a preferred embodiment, at least one or more water soluble solvents is selected from glycerin, ethylene glycol, propylene glycol, butylene glycol, or a combination thereof. Preferably, one of the one or more water soluble solvents I glycerin. When glycerin is present as one of the one or more water soluble solvents (or the only water soluble solvent), it may be present in an amount from about 5 to about 50 wt. %, based on a total weight of the unfoamed cleansing composition. In further embodiments, glycerin is in an amount of about 5 to about 45 wt. % about 10 to about 50 wt. %, about 10 to about 45 wt. %, about 15 to about 50 wt. %, about 15 to about 45 wt. %, about 20 to about 50 wt. %, about 20 to about 45 wt. %, about 25 to about 50 wt. %, about 25 to about 45 wt. %, about 30 to about 50 wt. %, about 30 to about 45 wt. %, about 35 to about 50 wt. %, or about 35 to about 45 wt. %, based on a total weight of the unfoamed cleansing composition.

(e) Water

The total amount of water in the stable foamed cleansing compositions can vary. Nonetheless, in various embodiments, the cleansing composition includes about 15 to about 55 wt. % water based on a total weight of the unfoamed cleansing composition. In further embodiments, the stable foamed cleansing composition includes about 15 to about 50 wt. %, about 15 to about 45 wt. %, about 20 to about 65 wt. %, about 20 to about 60 wt. %, about 20 to about 55 wt. %, about 20 to about 50 wt. %, about 20 to about 45 wt. %, about 25 to about 65 wt. %, about 25 to about 60 wt. %, about 25 to about 55 wt. %, about 25 to about 50 wt. %, about 25 to about 45 wt. %, about 30 to about 65 wt. %, about 30 to about 60 wt. %, about 30 to about 55 wt. %, about 30 to about 50 wt. %, about 30 to about 45 wt. %, about 35 to about 65 wt. %, about 35 to about 60 wt. %, about 35 to about 55 wt. %, about 35 to about 50 wt. %, or about 35 to about 45 wt. % of water based on a total weight of the unfoamed cleansing composition.

Ratio of (d):(e)

The weight ratio of the one or more water soluble solvents of (d) to the water of (e) will vary but is typically from about 0.5:1 to 5:1 ((d):(e)). In further embodiments, the weight ratio of (d) to (e) is about 0.5:1 to about 4:1, about 0.8:1 to about 5:1, about 0.8:1 to about 4:1, about 1:1 to about 5:1, about 1:1 to about 4:1, or about 1:1 to about 3:1. In further embodiments, the weight ratio of (d) to (e) is about 1:1 to about 6:1, about 1:1 to about 5:1, about 1:1 to about 4:1, about 1:1 to about 3:1, or about 1:1 to about 2:1.

(f) Salts Providing Monovalent Cations

The stable foamed cleansing composition may optionally include one or more salts providing monovalent cations. The salts providing monovalent cations are typically water soluble inorganic or organic salts with a molecular weight of less than 500. Nonlimiting examples include alkali metal salts. More specific but nonlimiting examples include sodium chloride, potassium chloride, sodium sulfate, and potassium sulfate. Sodium chloride is a particularly useful monovalent cation source.

If present, the total amount of the one or more salts providing monovalent cations may be from about 0.05 to about 2 wt. %, based on a total weight of the unfoamed cleansing composition. The total amount of the one or more salts providing monovalent cations may be from about 0.05 to about 1.8 wt. %, about 0.05 to about 1.5 wt. %, about 0.05 to about 1.2 wt. %, about 0.05 to about 1 wt. %, about 0.1 to about 2 wt. %, about 0.1 to about 1.5 wt. %, about 0.1 to about 1.2 wt. %, about 0.1 to about 1 wt. %, about 0.2 to about 2 wt. %, about 0.2 to about 1.5 wt. %, about 0.2 to about 1.2 wt. %, about 0.2 to about 1 wt. %, about 0.5 to about 2 wt. %, about 0.5 to about 1.5 wt. %, about 0.5 to about 1.2 wt. %, about 0.5 to about 1 wt. %, about 0.8 to about 2 wt. %, about 0.8 to about 1.5 wt. %, or about 0.8 to about 1.2 wt. %, based on a total weight of the unfoamed cleansing composition.

(g) Miscellaneous Ingredients

The stable foamed cleansing compositions may optionally include one more miscellaneous ingredients. Miscellaneous ingredients are ingredients that are compatible with the stable foamed cleansing compositions and do not disrupt or materially affect the basic and novel properties of the compositions. Nonlimiting examples of miscellaneous ingredients include preservatives, fragrances, pH adjusters, miscellaneous salts, chelating agents, skin active ingredients, buffers, antioxidants, flavonoids, depigmenting agents, anti-wrinkle agents, vitamins, botanical extracts, UV filtering agents, proteins, protein hydrolysates and/or isolates, fillers (e.g., organic and/or inorganic fillers such as talc, silica, etc.) composition colorants, etc.

In the context of the instant disclosure, a "composition colorant" is a compound that colors the composition but does not have an appreciable coloring effect on hair or skin. In other words, the composition colorant is included to provide a color to the stable foamed cleansing composition for aesthetic appeal but is not intended to impart coloring properties to hair or skin. As an example, hair styling gels can be found in a variety of different colors (e.g., light blue, light pink, etc.) yet application of the styling gel to hair does not visibly change the color of the hair.

Nonlimiting examples of antioxidants, skin active agents, depigmenting agents, and anti-wrinkle agents are set forth below.

(i) Antioxidants

Examples of antioxidants include tocopherols (e.g., d-α-tocopherol, d-β-tocopherol, d-γ-tocopherol, d-delta-tocopherol), tocotrienols (e.g., d-α-tocotrienol, d-β-tocotrienol, d-γ.-tocotrienol, d-delta-tocotrienol,) and vitamin E (α-tocopherol acetate). These compounds may be isolated from natural sources, prepared by synthetic means, or combinations thereof. Tocotrienol-enriched vitamin E preparations may be obtained by fractionating vitamin E preparations to remove a portion of tocopherols and recover a preparation more highly concentrated in tocotrienol. Useful tocotrienols are natural products isolated, for example, from wheat germ oil, grain, or palm oil using high performance liquid chromatography, or isolated by alcohol extraction and/or molecular distillation from barley, brewer's grain or oats. As used herein, the term "tocotrienols" includes tocotrienol-rich-fractions obtained from these natural products as well as the pure compounds. The increased glutathione peroxidase activity protects the skin from oxidative damage.

Vitamin C and derivatives may be used, including ascorbic acid, sodium ascorbate, and the fat soluble esters tetrahexyldecyl ascorbate and ascorbyl palmitate, magnesium ascorbyl phosphate, ascorbyl-glucoside, glucosamine ascorbate, ascorbyl acetate, etc. Additionally, extracts from plants containing a high amount of vitamin C such as camu berry (*Myrciaria dubia*), acerola, *Emblica officinalis*, and bioflavonoids from rose hip and citrus may be used including water soluble bioflavonoids such as hesperidin methyl chalcone may also be used.

Sesame (*Sesamum indicum*) or sesame lignan may also be added. Sesame and its lignans (the fibrous compounds associated with the sesame) act as antioxidants. Sesame seed lignans significantly enhance vitamin E activity.

In addition, carotenoids, particularly the xanthophyll type, are also useful antioxidants that can be used. The xanthopyll type carotenoids include molecules, such as lutein, canthaxantin, cryptoxanthin, zeaxanthin and astaxanthin. Xanthophylls protect compounds, such as vitamin A, vitamin E, and other carotenoids.

Flavonoids can also function as antioxidants. In some instances, the flavonoid is a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin. The flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin. The flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin. The flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol. The flavonoid may be a flavan-4-ol (derivative of 2-phenylchroman-4-ol). Flavan-4-ols include: Apiforol and Luteoforol. The flavonoid may be an isoflavone (derivative of 3-phenylchromen-4-one). Isoflavones include: Genistein, Daidzein, Biochanin A, Formononetin, and the Equol metabolite from Daidzein.

The antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

The antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

The antioxidant may be an anthocyanin. Anthocyanins and their derivatives are antioxidants. Anthocyanins encompasses a class of flavonoid compounds that are naturally occurring, water-soluble compounds, responsible for the red, purple, and blue colors of many fruits, vegetables, cereal grains, and flowers. Additionally, anthocyanins are collagenase inhibitors. The inhibition of collagenase helps in the prevention and reduction of wrinkles, increase in skin elasticity, etc., which are caused by a reduction in skin collagen. The anthocyanins may be obtained from any portion of various plant sources, such as the fruit, flower, stem, leaves, root, bark, or seeds. One of skill in the art will understand that certain portions of the plant may contain higher natural levels of anthocyanins, and, therefore, those portions are used to obtain the desired anthocyanins. In some instances, antioxidants may include one or more betacyanin. Betacyanins, like anthocyanins, may be obtained from natural sources and are antioxidants.

The antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

The antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C, and synthetic Safalcone.

The antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin.

The antioxidant may be a Tannin. Tannins include: Tannin, Terflavin B, Glucogallin, Dgallic acid, and Quercitannic acid.

The antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof.

The antioxidant may be a Coumarin (derivatives of 2H-chromen-2-one). Coumarins include: 4-Hydroxycoumarin, Umbelliferone, Aesculetin, Herniarin, Auraptene, and Dicoumarol.

The antioxidant may be a Carotenoid. Carotenoids include: beta-Carotene, alpha-Carotene, gamma-Carotene, beta-Cryptoxanthin, Lycopene, Lutein, and Idebenone. Sesame (*Sesamum indicum*) or sesame lignan may also be added. Sesame and its lignans (the fibrous compounds associated with the sesame) act as antioxidants. Sesame seed lignans significantly enhance vitamin E activity.

The antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

(ii) Skin Active Agents

Nonlimiting examples of skin active agents include hydroxyacetophenone, madecassoside, retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate; —derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris*, all marketed for example by Maruzen—extracts of meadowsweet (*Spiraea ulmaria*), such as that sold under the name Sebonormine by Silab—extracts of the alga *Laminaria saccharina*, such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of Terminalia chebula, nasturtium and of bioavailable zinc (microalgae), such as that sold under the name Seborilys Green Tech; —extracts of *Pygeum afrianum* such as that sold under the name *Pygeum afrianum* sterolic lipid extract by Euromed—extracts of *Serenoa serrulata* such as those sold under the name Viapure *Sabal* by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata*, such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of *cinchona* bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and combinations thereof.

(iii) Depigmenting Agents

Nonlimiting examples of depigmenting agents include alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, certain compounds derived from plants such as chamomile, bearberry, the aloe family (*vera, ferox, bardensis*), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

(iv) Anti-Wrinkle Agent

The term "anti-wrinkle agent" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Nonlimiting examples of anti-wrinkle agents include: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and combinations thereof. Examples of such compounds are: adenosine and its derivatives and retinoids other than retinol (as discussed above, such as retinol palmitate), ascorbic acid and its derivatives such as magnesium ascorbyl phosphate and ascorbyl glucoside; nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the a-hydroxy acids, b-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and combinations thereof. In at least one case, the skin tightening composition includes adenosine derivatives, such as non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside. Other derivatives include adenosine receptor agonists such as adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5' (N-cyclopropyl)-carboxamidoadenosine, DPMA (PD 129.944) and metrifudil.

As already noted, skin active agents may be included as one or more of the miscellaneous ingredients. With respect to the total amount of skin active agents in the cosmetic compositions, if present, the total amount of skin active agents may be from greater than zero to about 9 wt. %, greater than zero to about 8 wt. %, greater than zero to about 7 wt. %, greater than zero to about 6 wt. %, greater than zero to about 5 wt. %, greater than zero to about 4 wt. %, greater than zero to about 3 wt. %, greater than zero to about 2 wt. %; about 10 ppm to about 10 wt. % (100,000 ppm), about 10 ppm to about 5 wt. % (50,000 ppm), about 10 ppm to about 2.5 wt. % (25,000 ppm), about 10 ppm to about 1 wt. % (10,000 ppm), about 10 ppm to about 0.5 wt. % (5,000 ppm), about 10 ppm to about 0.3 wt. % (3,000 ppm), about 10 ppm to about 0.2 wt. % (2,000 ppm), about 10 ppm to about 0.1 wt. % (1,000 ppm), about 10 ppm to 500 ppm; about 0.1 to about 10 wt. %, about 0.1 to about 5 wt. %, about 0.1 to about 2.5 wt. %, about 0.1 to about 1 wt. %, about 0.1 to about 0.5 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, or about 4 to about 6 wt. %, based on the total weight of the cosmetic composition.

The total amount of the one or more miscellaneous ingredients, if present, will vary. Nonetheless, in various embodiments, the compositions include from about 0.001 to about 10 wt. % of one or more miscellaneous ingredients, based on the total weight of the composition. In further embodiments, the compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the composition.

Additional Embodiments

In various embodiments, the stable foamed cleansing compositions may optionally include one or more amphoteric surfactants. Nonetheless, the stable foamed cleansing composition do not require amphoteric surfactants and in other embodiments, the stable foamed cleansing composition is free or essentially free from amphoteric surfactants. Nonlimiting examples of amphoteric surfactants and amounts are provided below, under the heading "Amphoteric Surfactants."

The stable foamed cleansing compositions include one or more nonionic emulsifiers having a HLB of about 6 or less, as already discussed above. For purposes of the instant disclosure, the term "nonionic emulsifier" and "nonionic surfactant" are used interchangeably. Nonetheless, in various embodiments, the stable foamed cleansing compositions may include one or more additional nonionic surfactants having an HLB of greater than 6. In other embodiments, however, the stable foamed cleansing composition is free or essentially free from nonionic surfactants having an HLB of greater than 6. Nonlimiting examples of nonionic surfactants and amounts are provided below, under the heading "Nonionic Surfactants."

The one or more magnesium salts and the one or more acyl glycinate surfactants interact to provide thickening effects and stabilization to the foamed cleansing compositions. The addition of one or more salts providing monovalent cations can further enhance thickening and therefore may optionally be included in the stable foamed cleansing composition. Nonetheless, in various embodiments, one or more additional thickening agents may optionally be included in the stable foamed cleansing compositions. For purposes of the instant disclosure, the term "additional thickening agents" or simply "thickening agents" is used to refer to thickening agents other than the one or more acyl glycinate surfactants, the one or more magnesium salts, and the one or more salts providing monovalent cations. For example, nonlimiting examples of additional thickening agents include thickening polymers (e.g., anionic, cationic, amphoteric, and/or nonionic thickening polymers) and non-polymeric thickening agents such as clays (smectite, hectorite, montmorillonite, etc.). More specific but nonlimiting examples of additional thickening agents are provided below, under the heading "Additional Thickening Agents."

As described above, the stable foamed cleansing compositions typically include one or more water soluble solvents. Monoalcohols having from 2 to 6 carbon atoms are encompassed by the term water soluble solvents and may optionally be included in the stable foamed cleansing compositions. Nonetheless, in various embodiments, it is preferably for the stable foamed cleansing composition to be free or essentially free from ethanol, isopropanol, and mixtures thereof. In further embodiments, the stable foamed cleansing composition is free or essentially free from linear or branched monoalcohols having from 2 to 6 carbon atoms.

In various embodiments, the stable foamed includes one or more non-silicone fatty compounds. The term "non-silicone fatty compound" means a fatty compound that does not containing any silicon atoms (Si). Nonlimiting examples of non-silicone fatty compounds include oils, fatty alcohols, fatty acids, fatty alcohol, esters of fatty alcohols, hydroxy-substituted fatty acids, waxes, triglyceride compounds, lanolin, and a mixture thereof. In various embodiments, the stable foamed cleansing compositions includes one or more fatty alcohols, especially those having from about 10 to about 30 carbon atoms, from about 12 to about 22 carbon atoms, or from about 16 to about 22 carbon atoms. In other embodiments, the stable foamed cleansing compositions are free or essentially free from fatty alcohols. In various embodiments, the stable foamed cleansing compositions includes one or more fatty acids. Nonlimiting examples include those having from about 10 to about 30 carbon atoms, from about 12 to about 22 carbon atoms, or from about 16 to about 22 carbon atoms. In other embodiments, the stable foamed cleansing compositions are free or essentially free from fatty acids.

In a preferred embodiment, the stable foamed cleansing composition is free or essentially free from non-silicone fatty compounds. Similarly, in various embodiments, the stable foamed cleansing composition is free or essentially free from oil. In another embodiments, the stable foamed cleansing composition is free or essentially free from waxes. In another embodiment, the stable foamed cleansing composition is free or essentially free fatty alcohols. In another embodiment, the stable foamed cleansing composition is free or essentially free is free or essentially free from fatty acids.

Silicones such as silicone oils, silicone-containing emulsifiers, amino-functionalized silicones are useful in cosmetic compositions including cleansing compositions to provide, for example, conditioning and smoothing properties to hair or skin. Therefore, in certain embodiments, the stable foamed cleansing composition optionally include one or more silicones. In other embodiments, however, the stable foamed cleansing compositions are free or essentially free from silicones. The term "silicones" refers to synthetic compounds, of which silicon (Si) is a key element. For example, it includes synthetic polymers that are based on a framework of alternating silicon and oxygen (siloxane) bonds with at least one organic group attached to the silicon atom via a direct carbon-silicon bond. It also includes silicone emulsifiers (also referred to as "silicone-based emulsifiers"). Nonlimiting examples of silicone emulsifiers include PEG/PPG-18/18 dimethicone, PEG/PPG-18/18 dimethicone, cetyl PEG/PPG-10/1 dimethicone, PEG/PPG-18/18 dimethicone, PEG-9 dimethicone, and PEG-12 dimethicone. Nonlimiting examples of silicones also include dimethicone, dimethiconol, cyclomethicone, polysilicone-11, phenyl trimethicone, amodimethicone, trimethylsilylamodimethicone, and stearoxytrimethylsilane.

In various embodiments, the stable foamed cleansing composition optionally includes one or more cationic conditioning polymers. As the name suggests, the cationic conditioning polymers have a cationic charge and provide conditioning benefits to the hair or skin. Cationic conditioning polymers are not required and therefore, in various embodiments, the stable foamed cleansing composition is free or essentially free from cationic conditioning polymers Nonlimiting examples of cationic conditioning polymers include cationic polysaccharides derivatives, cationic gum derivatives, polymer derivatives of diallyldimethyl ammonium chloride, polymer derivatives of methacrylamidopropyltrimethylammonium chloride, cationic cellulose derivatives, quaternized hydroxyethyl cellulose, cationic starch derivatives, cationic guar gum derivatives (hydroxypropyl guar hydroxypropyltrimonium chloride), copolymers of acrylamide and dimethyldiallyammonium chloride, polyquaterniums, and a mixture thereof. A more exhaustive but nonlimiting list of cationic conditioning polymers is included later, under the heading "Cationic Conditioning Polymers."

Amphoteric Surfactants

The stable foamed cleansing composition optionally include one or more amphoteric surfactants. Nonetheless, amphoteric surfactants are not required and in various embodiments, the stable foamed hair cleansing composition is free or essentially free from amphoteric surfactants. Nonlimiting examples of amphoteric surfactants include alkyl amphoproprionates, betaines, alkyl sultaines, alkyl amphoacetates, and combinations thereof. In some instances, it is preferable to include one or more alkyl betaines.

Nonlimiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a combination thereof. Nonlimiting examples of betaines include coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof. Nonlimiting examples of alkyl sultaines include cocamidopropyl hydroxysultaine and lauryl hydroxysultaine. A nonlimiting example of an alkyl amphoacetate is sodium lauroamphoacetate.

If present, the one or more amphoteric surfactants may be in an amount from about 0.1 to about 10 wt. %, based on a total weight of the pre-foamed cleansing composition. In further embodiments, the stable foamed cleansing composition includes from about 0.1 to about 6 wt. %, about 0.5 to about 10 wt. %, about 0.5 to about 5 wt. %, about 1 to about 10 wt. %, or about 1 to about 5 wt. % of one or more amphoteric surfactants.

Nonionic Surfactants

The stable foamed cleansing compositions optionally include one or more nonionic surfactants other than the one or more nonionic emulsifiers having an HLB of about 6 or less. In other words, the stable foamed cleansing compositions optionally include one or more nonionic surfactants having an HLB of greater than 6. In other embodiments, however, the stable foamed cleansing compositions are free or essentially free form nonionic surfactants other than one or more nonionic emulsifiers having and HLB of about 6 or less. The following, nonlimiting examples of nonionic surfactants include nonionic surfactants having an HLB of about 6 or less and nonionic surfactants having an HLB of greater than 6. They are provided to provide examples of the various types of nonionic surfactants useful in the stable foamed cleansing compositions. Their HLB will determine whether they are further characterized as nonionic surfactants having an HLB of about 6 or less or nonionic surfactants having an HLB of greater than 6.

Nonlimiting examples of nonionic surfactants include: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$) acylaminopropylmorpholine oxides; and combinations thereof.

Nonlimiting examples of poly glucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred. Nonetheless, in various embodiments, the stable foamed cleansing composition is free or essentially free from poly glucosides. If present, the total amount of the one or more alkyl polyglucosides in the stable foamed cleansing compositions will vary but is typically from about 0.1 to about 10 wt. %, based on a total weight of the pre-foamed cleansing composition. In further embodiments, the stable foamed cleansing composition includes from about 0.1 to about 6 wt. %, about 0.5 to about 10 wt. %, about 0.5 to about 5 wt. %, about 1 to about 10 wt. %, or about 1 to about 5 wt. % of one or more nonionic surfactants.

Nonionic surfactants also include ethoxylated, propoxylated, and/or glycerolated surfactants having at least one fatty chain comprising, for example, from 8 to 18 carbon atoms. The number of ethylene oxide or propylene oxide groups may range from 2 to about 200, from 2 to 150, from 2 to 100, or from 2 to 50, and for the number of glycerol groups may range from 1 to 100, from 1 to 50, or from 1 to 30.

Nonionic surfactants include esters of polyols with fatty acids having a saturated or unsaturated chain comprising, for example, from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and combinations thereof.

Nonlimiting examples of ethoxylated fatty esters include the adducts of ethylene oxide with esters of lauric acid, palmitic acid, stearic acid or behenic acid, and combinations thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; and polyethylene glycol 100 EO monostearate (PEG-100 stearate). Nonlimiting examples of glyceryl esters of $C_8$-$C_{24}$ alkoxylated fatty acids include polyethoxylated glyceryl stearate (glyceryl mono-, di- and/or tristearate) such as PEG-20 glyceryl stearate.

If present, the total amount of the one or more nonionic surfactants having an HLB of greater than 6 will vary but may be in an amount from about 0.01 to about 10 wt. %, based on a total weight of the pre-foamed cleansing composition. In further embodiments, the stable foamed cleansing composition includes from about 0.01 to about 5 wt. %, about 0.01 to about 3 wt. %, about 0.1 to about 10 wt. %, about 0.1 to about 5 wt. %, about 0.1 to about 3 wt. %, about 1 to about 10 wt. %, about 1 to about 5 wt. %, or about 1 to about 3 wt. %, of the one or more nonionic surfactants having an HLB of greater than 6.

Additional Thickening Agents

The cleansing compositions may optionally include one or more thickening agents (also referred to as thickeners or viscosity modifying agents). As mentioned earlier, the term "additional thickening agents" or simply "thickening agents" is used to refer to thickening agents that increase viscosity of the stable foamed cleansing composition other than the magnesium salts providing divalent cations, the salts providing monovalent cations, and the acyl glycinate surfactants. These salts (or the cations from the salts) interact with the one or more acyl glycinate surfactants and can cause thickening to the cleansing compositions. Nonetheless, for purposes of the instant disclosure these salts and the one or more acyl glycinate surfactants are referred to as "salts" providing cations or "acyl glycinate surfactants" (not as thickening agents) to differentiate between them and other ingredients that can function to thicken the cleansing compositions.

The stable foamed hair cleansing composition optionally include one or more additional thickening agent, but additional thickening agents are not typically required. In fact, in various preferred embodiments, the stable foamed cleansing composition is free or essentially free from additional thickening agents.

Many thickening agents are water soluble and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water. Nonlimiting types of additional thickening polymers include carboxylic acid polymers, crosslinked polyacrylate polymers, polyacrylamide polymers, polysaccharides, and gums.

Carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Nonlimiting examples include acrylates/C10-C30 alkyl acrylate crosspolymers, carbomers, and the like.

Crosslinked polyacrylate polymers can be useful as thickening agents, for example, sodium polyacrylate. The crosslinked polyacrylate polymers may be cationic or nonionic Polyacrylamide polymers include polyacrylamide polymers with substituted, branched, or unbranched polymers. Other useful polyacrylamide polymers include multi-block copolymers of acrylamides and substituted acrylamides with acrylic acids and substituted acrylic acids.

A wide variety of polysaccharides can optionally be included in the stable foamed cleansing compositions. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and combinations thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Other useful polysaccharides include scleroglucans comprising a linear chain of (1-3) linked glucose units with a (1-6) linked glucose every three units, a commercially available example of which is Clearogel™. CS11 from Michel Mercier Products Inc.

The one or more additional thickening agent may include or be selected from gums, for example, gums primarily derived from natural sources. Nonlimiting examples include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and biosacharide gum.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

If present, the total amount of the one or more additional thickening agents will vary but may be in an amount from about 0.01 to about 6 wt. %, based on a total weight of the pre-foamed cleansing composition. In some instances, the total amount of the one or more additional thickening agents is from about 0.01 to about 5 wt. %, about 0.01 to about 3 wt. %, about 0.01 to about 2 wt. %, about 0.01 to about 1 wt. %, about 0.05 to about 6 wt. %, from about 0.05 to about 5 wt. %, from about 0.05 to about 3 wt. %, about 0.05 to 2 wt. %, about 0.05 to 1 wt. %, from 0.1 to about 6 wt. %, about 0.1 to about 5 wt. %, about 0.1 to about 3 wt. %, about 0.1 to about 2 wt. %, or about 0.1 to about 1 wt. %, based on the total weight of the pre-foamed cleansing composition.

Non-Silicone Fatty Compounds

The term "non-silicone fatty compound" means a fatty compound that does not contain any silicon atoms (Si). Non-limiting examples of non-silicone fatty compounds include oils, mineral oil, fatty alcohols, fatty acids, fatty alcohol derivatives, fatty acid derivatives, esters of fatty alcohols, hydroxy-substituted fatty acids, waxes, triglyceride compounds, lanolin, or a combination thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a combination thereof. In some cases, the fatty alcohols are those selected from the group consisting of cetyl alcohol, stearyl alcohol, isostearyl alcohol, oleyl alcohol, and a combination thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a combination thereof. In some cases, the fatty acids are selected from the group consisting of palmitic acid, stearic acid, and a combination thereof.

In some instance, the one or more non-silicone fatty compounds include one or more non-silicone oils. The term "oil" as used herein describes any material which is substantially insoluble in water and substantially liquid at room temperature (25° C.). The oils may be natural oil, synthetic oils, hydrocarbon-based oils, etc., but natural oils are often desired. Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a combination thereof. In some cases, soybean oil may be particularly useful.

The total amount of non-silicone fatty compounds, if present, can vary but are typically in an amount of about 0.001 to about 10 wt. %, based on the total weight of the cleansing composition. In some cases, the total amount of non-silicone fatty compounds is about 0.005 to about 5 wt. %, about 0.005 to about 3 wt. %, about 0.01 to about 10 wt. %, about 0.01 to about 5 wt. %, about 0.01 to about 3 wt. %, or about 0.01 to about 1 wt. % of the one or more non-silicone fatty compounds, based on the total weight of the cleansing composition.

Cationic Conditioning Polymers

Nonlimiting examples of cationic polymers include copolymers of 1-vinyl-2-pyrrolidine and 1-vinyl-3-methyl-imidazolium salt (e.g., chloride salt) (referred to as Polyquaternium-16); copolymers of 1-vinyl-2-pyrrolidine and dimethylaminoethyl methacrylate (referred to as Polyquaternium-11); cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). Additionally or alternatively, the cationic conditioning polymers may include or be chosen from cationic guar gum derivatives, such as guar hydroxypropyltrimonium chloride.

In certain embodiments, the one or more cationic conditioning polymers include cationic polysaccharide polymers, such as cationic cellulose, cationic starch, and cationic guar gum. In the context of the instant disclosure cationic polysaccharide polymers include cationic polysaccharides and polysaccharide derivatives (e.g., derivatized to be cationic), for example, resulting in cationic cellulose (cellulose derivatized to be cationic), cationic starch (derivatized to be cationic), cationic guar (guar derivatized to be cationic).

Non-limiting examples of cationic celluloses include hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, polyquaternium-10, polyquaternium-24, and mixtures thereof, preferably polyquaternium-10, polyquaternium-24, and mixtures thereof.

Non-limiting examples of cationic guar include guar hydroxypropyltrimonium chloride, hydroxypropyl guar hydroxypropyltrimonium chloride, Non-limiting examples of cationic starch include starch hydroxypropyltrimonium chloride, hydroxypropyl oxidized starch PG trimonium chloride, and a mixture thereof.

In various embodiments, the one or more cationic conditioning polymers are chosen from polyquaterniums. Non-limiting examples include Polyquaternium-1 (ethanol, 2,2',2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N', N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In various embodiments, the one or more cationic conditioning polymers are chosen from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful. A particularly preferred and useful cationic polymer is polyquaternium-10.

The cationic polymers may be a polyquaternium. In certain embodiments, the cationic surfactants may be polyquaterniums selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

In some embodiments, the one or more cationic conditioning polymers are chosen from cationic proteins and cationic protein hydrolysates (e.g., hydroxypropyltrimonium hydrolyzed wheat protein), quaternary diammonium polymers (e.g., hexadimethrine chloride), copolymers of acrylamide and dimethyldiallyammonium chloride, and mixtures thereof.

If present, the total amount of the one or more cationic conditioning polymer will vary but may be from about 0.01 to about 5 wt. %, based on a total weight of the pre-foamed cleansing composition. In further embodiments, the stable foamed cleansing composition includes from about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. %, based on a total weight of the pre-foamed cleansing composition.

Viscosity

The viscosity of the stable foamed cleansing compositions discussed throughout the instant disclosure will vary. Nonetheless, the stable foamed cleansing compositions typically have a viscosity similar to other cream/paste cleansing compositions, including facial cleansers, shampoo compositions, and some conditioning compositions. In certain embodiments, the viscosity of the stable foamed cleansing composition is from about 50 Pa-s to about 5,000 Pa-s at 25° C., the shear rate of 1 $s^{-1}$ (second). In further embodiments, the viscosity is from about 50 Pa-s to about 4,000 Pa-s, about 50 Pa-s to about 3,000 Pa-s, about 50 Pa-s to about 2,000 Pa-s, about 50 Pa-s to about 1,000 Pa-s, about 50 Pa-s to about 500 Pa-s, about 75 Pa-s to about 5,000 Pa-s, 75 Pa-s to about 4,000 Pa-s, about 75 Pa-s to about 3,000 Pa-s, about 75 Pa-s to about 2,000 Pa-s, about 75 Pa-s to about 1,000 Pa-s, about 75 Pa-s to about 500 Pa-s, about 100 Pa-s to about 5,000 Pa-s, 100 Pa-s to about 4,000 Pa-s, about 100 Pa-s to about 3,000 Pa-s, about 100 Pa-s to about 2,000 Pa-s, about 100 Pa-s to about 1,000 Pa-s, or about 100 Pa-s to about 500 Pa-s at 25° C., the shear rate of 1 $s^{-1}$. Preferably, the viscosity if from about 50 Pa-s to about 500 Pa-s at 25° C., the shear rate of 1 $s^{-1}$. The viscosity can be measured with a DHR-2 Rheometer.

pH

The pH of the stable foamed cleansing composition can vary but is typically from about 4 to about 8. In certain instances, it is preferable for the pH to be acidic or slightly acidic, having a pH of less than 7. Accordingly, in further embodiments, the pH of the stable foamed cleansing composition is from about 4 to about 7, about 4 to less than 7, about 4 to about 6.8, about 4 to about 6.6, about 5 to about 6.5, about 4.5 to about 7, about 4.5 to less than 7, about 4.5 to about 6.8, about 4.5 to about 6.6, about 4.5 to about 6.5, about 5 to about 7, about 5 to less than 7, about 5 to about 6.8, about 5 to about 6.6, or about 5 to about 6.5.

Preferred Embodiments

In a preferred embodiment, the stable foamed cleansing composition comprises, consists essentially of, or consists of (a) about 8 wt. % to about 40 wt. %, preferably about 10 to about 38 wt. %, more preferably about 12 to about 35 wt. % of one or more acyl glycinate surfactants, salts thereof, or combinations thereof, preferably wherein the one or more acyl glycinate surfactants are selected from sodium cocoyl glycinate, sodium lauroyl glycinate, sodium myristoyl glycinate, potassium lauroyl glycinate, potassium cocoyl glycinate, or mixtures thereof, more preferably wherein the one or more acyl glycinate surfactants comprises or consists of sodium cocoyl glycinate;

(b) about 0.5 to about 2 wt. % of one or more magnesium salts providing divalent cations having a charge density of about 40 to about 200 C/$mm^3$ and a water solubility of at least 400 g/L, preferably wherein the one or more magnesium salts are selected from magnesium chloride, magnesium sulfate, magnesium thiosulfate, magnesium pyrrolidone carboxylate (magnesium pidolate), magnesium gluconate, or mixtures thereof, more preferably wherein the one or more magnesium salts are selected from magnesium chloride, magnesium gluconate, or a combination thereof, more preferably wherein the one or more magnesium salts comprises or consists of magnesium chloride;

(c) about 2 wt. % to about 8 wt. %, preferably about 2 to about 7 wt. %, more preferably about 3 to about 7 wt. %, and even more preferably about 3 to about 6 wt. % of one or more nonionic emulsifiers having a Hydrophile-Lipophile Balance (HLB) of about 6 or less, preferably wherein the one or more emulsifiers having an HLB of 6 or less are selected from sorbitan esters, glyceryl esters, polyglyceryl esters, glycol esters, sucrose esters, methyl glucose esters, ethoxylated methyl glucose esters, or mixtures thereof, even more preferably wherein the one or more nonionic emulsifiers having an HLB of about 6 or less comprise or consist of one or more glycol esters, preferably selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, or mixtures thereof;

(d) about 25 to about 65 wt. %, preferably about 30 to about 55, more preferably about 35 to about 50 wt. %, and even more preferably about 35 to about 45 wt. % of one or more water soluble solvents, preferably wherein the one or more water soluble solvents are selected form glycerin, $C_2$-$C_6$ mono-alcohols, polyols, glycols, or mixtures thereof, more preferably wherein the one or more water soluble solvents are selected from glycerin, glycols, or mixtures thereof, and even more preferably wherein one of the one or more water soluble solvents is glycerin in an amount of at least 30 wt. %, preferably at least 35 wt. %, and even more preferably at least 38 wt. %; and (e) about 10 to about 55 wt. %, preferably from about 12 to about 45 wt. %, more preferably from about 15 to about 40 wt. %, and even more preferably about 20 to about 40 wt. % of water;

(f) optionally, about 0.1 to about 3 wt. %, preferably about 0.2 to about 2.5 wt. %, more preferably about 0.5 to about 2 wt. %, and even more preferably about 0.5 to about 1.5 wt. % of one or more one or more salts providing monovalent cations, wherein the one or salts providing monovalent cations are selected from sodium chloride, potassium chloride, sodium sulphate, potassium sulphate, ammonium chloride, monoethanolammonium chloride, or mixtures thereof, preferably wherein the one or more salts providing monovalent cations comprise or consist of sodium chloride;

(g) optionally, about 0.01 to about 10 wt. %, preferably about 0.1 to about 6 wt. %, more preferably about 1 to about 5 wt. % of one or more miscellaneous ingredients, preferably wherein the one or more miscellaneous ingredients are selected from preservatives, fragrances, pH adjusters, miscellaneous salts (other than (b) and (f), chelating agents, skin active ingredients, buffers, antioxidants, flavonoids, depigmenting agents, antiwrinkle agents, vitamins, botanical extracts, UV filtering agents, proteins, protein hydrolysates and/or isolates, fillers (e.g., organic and/or inorganic fillers such as talc, silica, etc.) composition colorants, additional thickening agents, amphoteric surfactants, nonionic surfactants having an HLB of greater than 6, cationic conditioning polymers, or mixtures thereof;

wherein the composition has a lamellar liquid crystal structure, the composition has been foamed by incorporation of an air or gas throughout the composition;

the composition has a specific gravity of about 0.6 to about 0.8 g/ml at 25° C., preferably about 0.65 to about 0.8 g/ml at 25° C., more preferably about 0.7 to about 0.8 g/ml at 25° C., and all percentages by weight are based on a total weight of the pre-foamed composition.

The weight ratio of the one or more water soluble solvents of (d) to the water of (e) may be from about 0.5:1 to 5:1 ((d):(e)). In preferred embodiments, the weight ratio of (d) to (e) is about 0.5:1 to about 4:1, about 0.8:1 to about 5:1, about 0.8:1 to about 4:1, about 1:1 to about 5:1, about 1:1 to about 4:1, or about 1:1 to about 3:1. In more preferred embodiments, the weight ratio of (d) to (e) is about 1:1 to about 6:1, about 1:1 to about 5:1, and especially about 1:1 to about 4:1.

The stable foamed cleansing composition is typically stable for at least 2 months in storage at 25° C. For example, the stable foamed cleansing composition substantially retains its original volume, i.e., the volume of the foamed cleansing composition immediately after preparation does not substantially change over time. For example, the stable foamed cleansing composition retains at least 90%, preferably at least 92%, more preferably at least 95 wt. % of its original volume after storage at 25° C. for at least 2 weeks, preferably after at least 4 weeks, more preferably after at least 2 months (or 8 weeks), even more preferably after at least 6 months (26 weeks).

The stable foamed cleansing composition has specific gravity of about 0.6 to about 0.8 g/ml at 25° C., preferably about 0.65 to about 0.8 g/ml at 25° C., more preferably about 0.7 to about 0.8 g/ml at 25° C. immediately upon manufacture and the specific gravity is maintained in the range of about 0.6 to about 0.8 g/ml at 25° C., preferably about 0.65 to about 0.8 g/ml at 25° C., more preferably about 0.7 to about 0.8 g/ml at 25° C., after storage at 25° C. for at least 2 weeks, preferably after at least 4 weeks, more preferably after at least 2 months (or 8 weeks), even more preferably after at least 6 months (26 weeks). Furthermore, in various embodiments, the specific gravity of the stable foamed cleansing composition immediately after manufacture does not change by more than 25%, preferably not more than 20%, more preferably not more than 15 wt. %, even more preferably not more than 10%, and ideally not more than 5% after storage at 25° C. for at least 2 weeks, preferably at least 4 weeks, more preferably at least 2 months (or 8 weeks), even more preferably after at least 6 months (26 weeks).

In another preferred embodiment, the stable foamed cleansing composition comprises, consists essentially of, or consists of (a) about 8 wt. % to about 40 wt. %, preferably about 10 to about 38 wt. %, more preferably about 12 to about 35 wt. % of one or more acyl glycinate surfactants comprising or consisting of sodium cocoyl glycinate;

(b) about 0.5 to about 2 wt. % of one or more magnesium salts providing divalent cations having a charge density of about 40 to about 200 C/mm$^3$ and a water solubility of at least 400 g/L, preferably wherein the one or more magnesium salts are selected from magnesium chloride, magnesium sulfate, magnesium thiosulfate, magnesium pyrrolidone carboxylate (magnesium pidolate), magnesium gluconate, or mixtures thereof, more preferably wherein the one or more magnesium salts are selected from magnesium chloride, magnesium gluconate, or a combination thereof, more preferably wherein the one or more magnesium salts comprises or consists of magnesium chloride;

(c) about 2 wt. % to about 8 wt. %, preferably about 2 to about 7 wt. %, more preferably about 3 to about 7 wt. %, and even more preferably about 3 to about 6 wt. % of one or more nonionic emulsifiers having a Hydrophile-Lipophile Balance (HLB) of about 6 or less, preferably wherein the one or more emulsifiers having an HLB of 6 or less are selected from sorbitan esters, glyceryl esters, polyglyceryl esters, glycol esters, sucrose esters, methyl glucose esters, ethoxylated methyl glucose esters, or mixtures thereof, even more preferably wherein the one or more nonionic emulsifiers having an HLB of about 6 or less comprise or consist of one or more glycol esters, preferably selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, or mixtures thereof;

(d) about 25 to about 65 wt. %, preferably about 30 to about 55, more preferably about 35 to about 50 wt. %, and even more preferably about 35 to about 45 wt. % of one or more water soluble solvents, preferably wherein the one or more water soluble solvents are selected form glycerin, $C_2$-$C_6$ mono-alcohols, polyols, glycols, or mixtures thereof, more preferably wherein the one or more water soluble solvents are selected from glycerin, glycols, or mixtures thereof, even more preferably wherein one of the one or more water soluble solvents are selected from ethylene glycol, propylene glycol, butylene glycol, hexylene glycol, pentylene glycol, diethylene glycol, dipropylene glycol, 1,3 propanediol, caprylyl glycol, glycerin, or mixtures thereof, and even more preferably wherein the one or more water soluble solvents comprises or consists of glycerin, ethylene glycol, propylene glycol, butylene glycol, hexylene glycol, diethylene glycol, dipropylene glycol, 1,3 propanediol, caprylyl glycol, or mixtures thereof in an amount of at least 30 wt. %, preferably at least 35 wt. %, and even more preferably at least 38 wt. %, even more preferably wherein the one or more water soluble solvents comprises or consists of glycerin in an amount of at least 30 wt. %, preferably at least 35 wt. %, and even more preferably at least 38 wt. %, (e) about 10 to about 55 wt. %, preferably from about 12 to about 45 wt. %, more preferably from about 15 to about 40 wt. %, and even more preferably about 20 to about 40 wt. % of water;

(f) optionally, about 0.1 to about 3 wt. %, preferably about 0.2 to about 2.5 wt. %, more preferably about 0.5 to about 2 wt. %, and even more preferably about 0.5 to about 1.5 wt. % of one or more one or more salts providing monovalent cations, wherein the one or salts providing monovalent cations are selected from sodium chloride, potassium chloride, sodium sulphate, potassium sulphate, ammonium chloride, monoethanolammonium chloride, or mixtures thereof, preferably wherein the one or more salts providing monovalent cations comprise or consist of sodium chloride;

(g) optionally, about 0.01 to about 6 wt. %, preferably about 0.05 to about 5 wt. %, more preferably about 0.1 to about 3 wt. % of one or more additional thickening agents;

(h) optionally, about 0.01 to about 8 wt. %, about 0.1 to about 6 wt. %, or about 1 to about 5 wt. % of one or more nonionic surfactants having an HLB of greater than 6;

(i) optionally, about 0.01 to about 8 wt. %, about 0.1 to about 6 wt. %, or about 1 to about 5 wt. % of one or more amphoteric surfactants;

(j) optionally, about 0.1 to about 10 wt. %, preferably about 0.5 to about 8 wt. %, more preferably about 0.5 to about 5 wt. % of one or more non-silicone fatty compounds; and (h) optionally, about 0.01 to about 10 wt. %, preferably about 0.1 to about 6 wt. %, more preferably about 1 to about 5 wt. % of one or more miscellaneous ingredients, preferably wherein the one or more miscellaneous ingredients are selected from preservatives, fragrances, pH adjusters, miscellaneous salts (other than (b) and (f), chelating agents, skin active ingredients, buffers, antioxidants, flavonoids, depigmenting agents, anti-wrinkle agents, vitamins, botanical extracts, UV filtering agents, proteins, protein hydrolysates and/or isolates, fillers (e.g., organic and/or inorganic fillers such as talc, silica, etc.) composition colorants, additional thickening agents, amphoteric surfactants, nonionic surfactants having an HLB of greater than 6, cationic conditioning polymers, or mixtures thereof;

wherein the composition has a lamellar liquid crystal structure, the composition has been foamed by incorporation of an air or gas throughout the composition;

the composition has a specific gravity of about 0.6 to about 0.8 g/ml at 25° C., preferably about 0.65 to about 0.8 g/ml at 25° C., more preferably about 0.7 to about 0.8 g/ml at 25° C., and all percentages by weight are based on a total weight of the pre-foamed composition.

The weight ratio of the one or more water soluble solvents of (d) to the water of (e) may be from about 0.5:1 to 5:1 ((d):(e)). In preferred embodiments, the weight ratio of (d) to (e) is about 0.5:1 to about 4:1, about 0.8:1 to about 5:1, about 0.8:1 to about 4:1, about 1:1 to about 5:1, about 1:1 to about 4:1, or about 1:1 to about 3:1. In more preferred embodiments, the weight ratio of (d) to (e) is about 1:1 to about 6:1, about 1:1 to about 5:1, and especially about 1:1 to about 4:1.

The stable foamed cleansing composition is preferably free or essentially free from silicones.

In certain embodiments, the stable foamed cleansing composition includes from about 0.01 to about 5, preferably about 0.05 to about 3, more preferably about 0.1 to about 1 wt. % of one or more cationic conditioning polymers.

The stable foamed cleansing composition is typically stable for at least 2 months in storage at 25° C. For example, the stable foamed cleansing composition substantially retains its original volume, i.e., the volume of the foamed cleansing composition immediately after preparation does not substantially change over time. For example, the stable foamed cleansing composition retains at least 90%, preferably at least 92%, more preferably at least 95 wt. % of its original volume after storage at 25° C. for at least 2 weeks, preferably after at least 4 weeks, more preferably after at least 2 months (or 8 weeks), even more preferably after at least 6 months (26 weeks).

The stable foamed cleansing composition has specific gravity of about 0.6 to about 0.8 g/ml at 25° C., preferably about 0.65 to about 0.8 g/ml at 25° C., more preferably about 0.7 to about 0.8 g/ml at 25° C. immediately upon manufacture and the specific gravity is maintained in the range of about 0.6 to about 0.8 g/ml at 25° C., preferably about 0.65 to about 0.8 g/ml at 25° C., more preferably about 0.7 to about 0.8 g/ml at 25° C., after storage at 25° C. for at least 2 weeks, preferably after at least 4 weeks, more preferably after at least 2 months (or 8 weeks), even more preferably after at least 6 months (26 weeks). Furthermore, in various embodiments, the specific gravity of the stable foamed cleansing composition immediately after manufacture does not change by more than 25%, preferably not more than 20%, more preferably not more than 15 wt. %, even more preferably not more than 10%, and ideally not more than 5% after storage at 25° C. for at least 2 weeks, preferably at least 4 weeks, more preferably at least 2 months (or 8 weeks), even more preferably after at least 6 months (26 weeks).

In another preferred embodiment, the stable foamed cleansing composition comprises, consists essentially of, or consists of (a) about 8 wt. % to about 40 wt. %, preferably about 10 to about 38 wt. %, more preferably about 12 to about 35 wt. % of one or more acyl glycinate surfactants comprising or consisting of sodium cocoyl glycinate;

(b) about 0.5 to about 2 wt. % of one or more magnesium salts selected from magnesium chloride, magnesium sulfate, magnesium thiosulfate, magnesium pyrrolidone carboxylate (magnesium pidolate), magnesium gluconate, or mixtures thereof, preferably wherein the one or more magnesium salts are selected from magnesium chloride, magnesium gluconate, or a combination thereof, more preferably wherein the one or more magnesium salts comprise or consists of magnesium chloride;

(c) about 2 wt. % to about 8 wt. %, preferably about 2 to about 7 wt. %, more preferably about 3 to about 7 wt. %, and even more preferably about 3 to about 6 wt. % of one or more nonionic emulsifiers having a Hydrophile-Lipophile Balance (HLB) of about 6 or less, preferably wherein the one or more emulsifiers having an HLB of 6 or less are selected from sorbitan esters, glyceryl esters, polyglyceryl esters, glycol esters, sucrose esters, methyl glucose esters, ethoxylated methyl glucose esters, or mixtures thereof, even more preferably wherein the one or more nonionic emulsifiers having an HLB of about 6 or less comprise or consist of one or more glycol esters, preferably selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, or mixtures thereof;

(d) about 25 to about 65 wt. %, preferably about 30 to about 55, more preferably about 35 to about 50 wt. %, and even more preferably about 35 to about 45 wt. % of one or more water soluble solvents selected from glycerin, polyols, glycols, or mixtures thereof, more preferably wherein the one or more water soluble solvents are ethylene glycol, propylene glycol, butylene glycol, hexylene glycol, pentylene glycol, diethylene glycol, dipropylene glycol, 1,3 propanediol, caprylyl glycol, glycerin, or mixtures thereof, and even more preferably wherein the one or more water soluble solvents comprises or consists of glycerin, ethylene glycol, propylene glycol, butylene glycol, 1,3 propanediol, or mixtures thereof in an amount of at least 30 wt. %, preferably at least 35 wt. %, and even more preferably at least 38 wt. %, even more preferably wherein the one or more water soluble solvents comprises or consists of glycerin in an amount of at least 30 wt. %, preferably at least 35 wt. %, and even more preferably at least 38 wt. %, (e) about 10 to about 55 wt. %, preferably from about 12 to about 45 wt. %, more preferably from about 15 to about 40 wt. %, and even more preferably about 20 to about 40 wt. % of water;

wherein (d) and (e) are in a weight ratio of about 0.8:1 to about 5:1, preferably about 0.9:1 to about 4:1, more preferably about 1:1 to 4:1, and even more preferably about 1:1 to 2:1 ((d):(e);

(f) about 0.1 to about 3 wt. %, preferably about 0.2 to about 2.5 wt. %, more preferably about 0.5 to about 2 wt. %, and even more preferably about 0.5 to about 1.5 wt. % of one or more one or more salts providing monovalent cations, wherein the one or salts providing monovalent cations are selected from sodium chloride, potassium chloride, sodium sulphate, potassium sulphate, ammonium chloride, monoethanolammonium chloride, or mixtures thereof, preferably wherein the one or more salts providing monovalent cations comprise or consist of sodium chloride;

(g) optionally, about 0.01 to about 10 wt. %, preferably about 0.1 to about 6 wt. %, more preferably about 1 to about 5 wt. % of one or more miscellaneous ingredients, preferably wherein the one or more miscellaneous ingredients are selected from preservatives, fragrances, pH adjusters, miscellaneous salts (other than (b) and (f), chelating agents, skin active ingredients, buffers, antioxidants, flavonoids, depigmenting agents, anti-wrinkle agents, vitamins, botanical extracts, UV filtering agents, proteins, protein hydrolysates and/or isolates, fillers (e.g., organic and/or inorganic fillers such as talc, silica, etc.) composition colorants, additional thickening agents, amphoteric surfactants, nonionic surfactants having an HLB of greater than 6, cationic conditioning polymers, or mixtures thereof;

wherein the composition has a lamellar liquid crystal structure, the composition has been foamed by incorporation of an air or gas throughout the composition;

the composition has a specific gravity of about 0.6 to about 0.8 g/ml at 25° C., preferably about 0.65 to about 0.8 g/ml at 25° C., more preferably about 0.7 to about 0.8 g/ml at 25° C., and all percentages by weight are based on a total weight of the pre-foamed composition.

The stable foamed cleansing composition is preferably free or essentially free from silicones.

The stable foamed cleansing compositions is preferably free or essentially free from linear or branched monoalcohols having from 2 to 6 carbon atoms, in particular, ethanol and/or isopropanol.

The stable foamed cleansing composition is typically stable for at least 2 months in storage at 25° C. For example, the stable foamed cleansing composition substantially retains its original volume, i.e., the volume of the foamed cleansing composition immediately after preparation does not substantially change over time. For example, the stable foamed cleansing composition retains at least 90%, preferably at least 92%, more preferably at least 95 wt. % of its original volume after storage at 25° C. for at least 2 weeks, preferably after at least 4 weeks, more preferably after at least 2 months (or 8 weeks), even more preferably after at least 6 months (26 weeks).

The stable foamed cleansing composition has specific gravity of about 0.6 to about 0.8 g/ml at 25° C., preferably about 0.65 to about 0.8 g/ml at 25° C., more preferably about 0.7 to about 0.8 g/ml at 25° C. immediately upon manufacture and the specific gravity is maintained in the range of about 0.6 to about 0.8 g/ml at 25° C., preferably about 0.65 to about 0.8 g/ml at 25° C., more preferably about 0.7 to about 0.8 g/ml at 25° C., after storage at 25° C. for at least 2 weeks, preferably after at least 4 weeks, more preferably after at least 2 months (or 8 weeks), even more preferably after at least 6 months (26 weeks). Furthermore, in various embodiments, the specific gravity of the stable foamed cleansing composition immediately after manufacture does not change by more than 25%, preferably not more than 20%, more preferably not more than 15 wt. %, even more preferably not more than 10%, and ideally not more than 5% after storage at 25° C. for at least 2 weeks, preferably at least 4 weeks, more preferably at least 2 months (or 8 weeks), even more preferably after at least 6 months (26 weeks).

In another preferred embodiment, the stable foamed cleansing composition comprises, consists essentially of, or consists of (a) about 8 wt. % to about 40 wt. %, preferably about 10 to about 38 wt. %, more preferably about 12 to about 35 wt. % of sodium cocoyl glycinate;

(b) about 0.5 to about 2 wt. % of magnesium chloride and optionally magnesium gluconate;

(c) about 3 to about 7 wt. %, preferably about 3 to about 6 wt. % of one or more glycol esters, preferably wherein the one or more glycol esters are selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, or mixtures thereof, more preferably wherein the one or more glycol esters comprise or consist of glycol distearate;

(d) about 35 to about 50 wt. %, preferably about 35 to about 45 wt, more preferably about 40 to about 45 wt. % of one or more water soluble solvents selected from glycerin, polyols, glycols, or mixtures thereof, wherein preferably the one or more water soluble solvents are selected from ethylene glycol, propylene glycol, butylene glycol, hexylene glycol, pentylene glycol, diethylene glycol, dipropylene glycol, 1,3 propanediol, caprylyl glycol, glycerin, or mixtures thereof, and even more preferably wherein the one or more water soluble solvents comprises or consists of glycerin in an amount of at least 30 wt. %, preferably at least 35 wt. %, and even more preferably at least 38 wt. %, (e) about 10 to about 55 wt. %, preferably from about 12 to about 45 wt. %, more preferably from about 15 to about 40 wt. %, and even more preferably about 20 to about 40 wt. % of water;

wherein (d) and (e) are in a weight ratio of about 0.8:1 to about 5:1, preferably about 0.9:1 to about 4:1, more preferably about 1:1 to 4:1, and even more preferably about 1:1 to 2:1 ((d):(e);

(f) about 0.2 to about 2.5 wt. %, preferably about 0.5 to about 2 wt. %, and more preferably about 0.5 to about 1.5 wt. % of one or more salts providing monovalent cations, wherein the one or salts providing monovalent cations are selected from sodium chloride, potassium chloride, sodium sulphate, potassium sulphate, ammonium chloride, monoethanolammonium chloride, or mixtures thereof, preferably wherein the one or more salts providing monovalent cations comprise or consist of sodium chloride;

(g) optionally, about 0.01 to about 10 wt. %, preferably about 0.1 to about 6 wt. %, more preferably about 1 to about 5 wt. % of one or more miscellaneous ingredients, preferably wherein the one or more miscellaneous ingredients are selected from preservatives, fragrances, pH adjusters, miscellaneous salts (other than (b) and (f), chelating agents, skin active ingredients, buffers, antioxidants, flavonoids, depigmenting agents, anti-wrinkle agents, vitamins, botanical extracts, UV filtering agents, proteins, protein hydrolysates and/or isolates, fillers (e.g., organic and/or inorganic fillers such as talc, silica, etc.) composition colorants, additional thickening agents, amphoteric surfactants, nonionic surfactants having an HLB of greater than 6, cationic conditioning polymers, or mixtures thereof;

wherein the composition has a lamellar liquid crystal structure, the composition has been foamed by incorporation of an air or gas throughout the composition;

the composition has a specific gravity of about 0.6 to about 0.8 g/ml at 25° C., preferably about 0.65 to about 0.8 g/ml at 25° C., more preferably about 0.7 to about 0.8 g/ml at 25° C., and all percentages by weight are based on a total weight of the pre-foamed composition.

The stable foamed cleansing composition is typically stable for at least 2 months in storage at 25° C. For example, the stable foamed cleansing composition substantially retains its original volume, i.e., the volume of the foamed cleansing composition immediately after preparation does not substantially change over time. For example, the stable foamed cleansing composition retains at least 90%, preferably at least 92%, more preferably at least 95 wt. % of its original volume after storage at 25° C. for at least 2 weeks, preferably after at least 4 weeks, more preferably after at least 2 months (or 8 weeks), even more preferably after at least 6 months (26 weeks).

The stable foamed cleansing composition has specific gravity of about 0.6 to about 0.8 g/ml at 25° C., preferably about 0.65 to about 0.8 g/ml at 25° C., more preferably about 0.7 to about 0.8 g/ml at 25° C. immediately upon manufacture and the specific gravity is maintained in the range of about 0.6 to about 0.8 g/ml at 25° C., preferably about 0.65 to about 0.8 g/ml at 25° C., more preferably about 0.7 to about 0.8 g/ml at 25° C., after storage at 25° C. for at least 2 weeks, preferably after at least 4 weeks, more preferably after at least 2 months (or 8 weeks), even more preferably after at least 6 months (26 weeks). Furthermore, in various embodiments, the specific gravity of the stable foamed cleansing composition immediately after manufacture does not change by more than 25%, preferably not more than 20%, more preferably not more than 15 wt. %, even more preferably not more than 10%, and ideally not more than 5% after storage at 25° C. for at least 2 weeks, preferably at least 4 weeks, more preferably at least 2 months (or 8 weeks), even more preferably after at least 6 months (26 weeks).

Methods

The stable foamed cleansing compositions of the instant disclosure are particularly useful for cleansing and hydrating/moisturizing hair and skin. Accordingly, the cleansing compositions are useful in methods for cleansing hair and skin, methods of conditioning hair and skin, and methods for imparting smoothness, moisturization, or hydration to the skin. The methods typically comprise application of the stable foamed cleansing composition to the hair or skin. The stable foamed cleansing compositions can be massed or spread throughout the hair or skin and subsequently rinsed from the hair or skin. In a preferred embodiment, the stable foamed cleansing composition are useful as a skin cleanser, for example, a skin cleanser for the face, i.e., a facial cleanser.

EXAMPLES

Various changes can be made in the above-described compositions and methods without departing from the scope of the invention. Accordingly, it is intended that all disclosure contained in the above description and in the examples given below, shall be interpreted as illustrative and not in a limiting sense.

Example 1

| | | | Inventive | | | | | Comparative | |
|---|---|---|---|---|---|---|---|---|---|
| | | | A | B | C | D | E | C-1 | C-2 |
| Acyl-Amino Acid Surfactant | (a) | SODIUM COCOYL GLYCINATE | 14 | 16 | 16 | 36 | 16 | 14.4 | 14.4 |
| Magnesium Salt | (b) | MAGNESIUM CHLORIDE | 0.6 | 0.6 | 0.6 | 0.6 | 1.5 | | |
| | | MAGNESIUM GLUCONATE | | | 0.5 | | 0.5 | | |
| Nonionic Emulsifier (HLB ≤ 6) | (c) | GLYCOL DISTEARATE (HLB = 5-6) | 3 | 6 | 6 | 6 | 3 | | 3 |
| Nonionic Emulsifier (HLB > 6) | | BEHENYL ALCOHOL (HLB = 16) | | | | | | 3 | |
| Water Soluble | (d) | GLYCERIN | 40 | 40 | 40 | 43 | 40 | 42 | 42 |
| Solvent | | CAPRYLYL GLYCOL [1] | 0.5 | 0.5 | 0.5 | 0.5 | 0.5 | 0.3 | 0.3 |
| Water | (e) | WATER | 40 | 35 | 34.5 | 12 | 36.6 | 36 | 36 |
| | Ratio of (d):(e) | | 1:1 | 1.2:1 | 1.2:1 | 3.6:1 | 1.1:1 | 1.2:1 | 1.2:1 |

-continued

| | | | Inventive | | | | | Comparative | |
|---|---|---|---|---|---|---|---|---|---|
| | | | A | B | C | D | E | C-1 | C-2 |
| Monovalent Cation | (f) | SODIUM CHLORIDE | 1 | 1 | 1 | 1 | 1 | | 1 |
| Thickening Polymers | | ACRYLATES COPOLYMER | | | | | | 1.1 | 1.1 |
| | | HYDROXYPROPYL STARCH PHOSPHATE | | | | | | | |
| | | CARBOPOL | | | | | | | |
| Misc.[2] | (g) | Miscellaneous | ≤5 | ≤5 | ≤5 | ≤5 | ≤5 | ≤5 | ≤5 |
| | | pH | ~6.6 | | | | | | |
| Pre-Foaming Viscosity [3] | | | 50-500 Pa-s | | | | | <50 Pa-s | |

[1] Caprylyl glycol acts as a preservative and therefore may be characterized as a preservative in the miscellaneous ingredients.
[2] For example, pH adjusters, fragrances, preservatives, antioxidants, chelating agents (e.g., tetrasodium glutamate diacetate), compositions colorants, fillers, humectants, emollients, skin-active agents such as hydroxyacetophenone, botanical extracts, etc.
[3] Measured at 25° C. with a DHR-2 Rheometer, shear rate 1 $s^{-1}$.

The examples above show that Comparative Compositions C-1 and C-2 had a viscosity less than 50 Pa-s, which is too low to be subsequently foamed into a stable product. The viscosity was too low despite the inclusion of a thickening polymer (acylates copolymers).

Example 2

| | | | Inventive | | | | | Comparative | | | | |
|---|---|---|---|---|---|---|---|---|---|---|---|---|
| | | | A | B | C | D | E | C-3 | C-4 | C-5 | C-6 | C-7 |
| Acyl-Amino Acid Surfactant | (a) | SODIUM COCOYL GLYCINATE | 14 | 16 | 16 | 36 | 16 | | 16 | 16 | 16 | 16 |
| | | POTASSIUM COCOYL GLYCINATE | | | | | | 14 | | | | |
| Magnesium Salt | (b) | MAGNESIUM CHLORIDE | 0.6 | 0.6 | 0.6 | 0.6 | 1.5 | 0.6 | 0.6 | 0.6 | 0.6 | 2 |
| | | MAGNESIUM GLUCONATE | | | 0.5 | | 0.5 | | | | 0.5 | 0.5 |
| Nonionic Emulsifier (HLB ≤ 6) | (c) | GLYCOL DISTEARATE (HLB = 5-6) | 3 | 6 | 6 | 6 | 3 | 3 | 3 | 3 | 8 | 3 |
| Water Soluble | (d) | GLYCERIN | 40 | 40 | 40 | 43 | 40 | 40 | 38 | 38 | 40 | 40 |
| Solvent | | CAPRYLYL GLYCOL | 0.5 | 0.5 | 0.5 | 0.5 | 0.5 | 0.5 | 0.5 | 0.5 | 0.5 | 0.5 |
| Water | (e) | WATER | 40 | 35 | 34.5 | 12 | 36.6 | 41 | 38 | 41 | 37 | 36.6 |
| Ratio of (d):(e) | | | 1:1 | 1.2:1 | 1.2:1 | 3.6:1 | 1.1:1 | 1:1 | 1:1 | 0.9:1 | 1:1 | 1.1:1 |
| Thickening Polymer | | ACRYLATES COPOLYMER | | | | | | | 6 | 3 | | |
| Monovalent Cation | (f) | SODIUM CHLORIDE | 1 | 1 | 1 | 1 | 1 | | 1 | 1 | 1 | 1 |
| Misc. [1] | (g) | Miscellaneous | ≤5 | ≤5 | ≤5 | ≤5 | ≤5 | ≤5 | ≤5 | ≤5 | ≤5 | ≤5 |
| pH | | | ~6.6 | | | | | | | | | |
| $T_0$ SPG Density g/mL | | | 0.78 | 0.8 | 0.8 | 0.83 | 0.81 | 0.85 | 1.06 | 1.03 | 0.92 | 0.87 |
| Stable @ 25° C. for 4 weeks | | | YES | | | | | NO | | | | |

[1] For example, pH adjusters, fragrances, preservatives, antioxidants, chelating agents (e.g., tetrasodium glutamate diacetate), compositions colorants, fillers, humectants, emollients, skin-active agents such as hydroxyacetophenone, botanical extracts, etc.
[2] Measured at 25° C. with a DHR-2 Rheometer at 25° C., shear rate 1 $s^{-1}$.

The data shows that when the specific gravity of the cleansing composition is higher than about 0.83, the foamed cleansing composition is not stable, even though high amounts of thickening polymer (acrylates copolymer) were included in the compositions. This is illustrated by the results for comparative compositions. Comparative composition C-6 also shows that when the amount of the nonionic emulsifier having an HLB of about 6 or less is higher than about 6 or about 7 wt. %, the foamed cleansing composition is not stable. Comparative composition C-7 shows that when the total amount of magnesium salts is above about 2 wt. %, the foamed cleansing composition was not stable.

The data in Example 1 and Example 2 illustrate the inventors' surprising discovery that glycinate surfactants uniquely interact with magnesium salts to thicken and stabilize the cleansing compositions. The amount of magnesium salts should be from about 0.5 to about 2 wt. % to achieve the surprising effects. Further, the inventors found that the nonionic emulsifiers having an HLB of about 6 or less should be in an amount of about 3 to about 7 wt. % to achieve the surprising effects. The combination and amounts of these components contribute to a specific gravity of about 0.6 to about 0.83, which the inventors surprisingly found is needed to ensure stability.

The foregoing disclosure illustrates and describes embodiments of the invention. The disclosure shows and describes only the preferred embodiments but it is understood that the invention is useable in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure. Accordingly, the description is not intended to limit the invention.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" or "a combination thereof" also relates to "mixtures thereof" or "combinations thereof." Throughout the disclosure, the term "a combination thereof" may be used following a list of elements as shown in the following example where letters A-F represent the elements: "one or more elements selected from the group consisting of A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from the group consisting of A, B, C, D, E, F, and a combination of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a combination thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The surfactants referred to throughout the disclosure may include those having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number. For example, an amount of "about 1 wt." can include an amount as low as 0.95 wt. % or as high as 1.05. Similarly, an amount of "about 50" can include an amount as low as 47.5 wt. % and as high as 52.5.

Some of the various categories of ingredients identified for the cleansing compositions may overlap. In such cases where overlap may exist and the composition/product includes two overlapping ingredients (or more than two overlapping ingredients), an overlapping ingredient does not represent more than one claimed component. For example, a fatty acid may be construed as both a "fatty compound" and separately as a "nonionic surfactant" or "nonionic emulsifier.' If a claimed composition/product refers to a fatty compound and separately to a nonionic surfactant, a single fatty acid in a composition will serve as only the fatty compound or as only the nonionic surfactant. A single fatty acids cannot simultaneously serve as both the fatty compound and the nonionic surfactant.

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactant" (or "emulsifier") includes salts of the surfactant, to the extent they exist, even if not explicitly stated. In other words, whenever the disclosure refers to a surfactant (or surfactants), it is intended that salts of the surfactants are also encompassed to the extent they exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded from the claims and from the compositions and methods described throughout the disclosure In other words, the cleansing compositions of the instant disclosure may be free or essentially free of any one or more of the components positively set forth in the instant disclosure for possible inclusion into the cleansing compositions.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of 1% or less by weight does not materially affect the basic and novel characteristics of the claimed invention). Similarly, when a composition is essentially free from a particular element, the composition may include 1 wt. % or less, 0.5 wt. % or less, 0.1 wt. % or less, 0.05 wt. % or less, 0.01 wt. % or less, or none of the specified material. For example, if a composition is "substantially free" or "essentially free" from ethanol, the composition may optionally include ethanol in an amount up to 1 wt. %, based on the total weight of the composition, provided an amount of 1 wt. % does not materially affect the basic and novel characteristics of the composition. Furthermore, the composition may optionally include 0.5 wt. % or less, 0.1 wt. % or less, 0.05 wt. % or less, 0.01 wt. % or less, or none of the ethanol.

All publications and patent applications cited throughout the disclosure are incorporated herein by reference in their entirety, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A stable foamed cleansing composition comprising:
(a) about 8 wt. % to about 40 wt. % of one or more acyl glycinate surfactants, salts thereof, or combinations thereof;
(b) about 0.5 to about 2 wt. % of one or more magnesium salts providing divalent cations having a charge density of about 40 to about 200 C/$mm^3$ and a water solubility of at least 400 g/L;
(c) about 3 wt. % to about 7 wt. % of one or more nonionic emulsifiers having a Hydrophile-Lipophile Balance (HLB) of about 6 or less;
(d) about 25 to about 65 wt. % of one or more water soluble solvents; and
(e) about 10 to about 55 wt. % of water;
wherein the composition has a lamellar liquid crystal structure,
the composition has been foamed by incorporation of an air or gas throughout the composition;
the composition has a specific gravity of about 0.6 about 0.8 g/mL at 25° C., and
all percentages by weight are based on a total weight of the pre-foamed composition.

2. The cleansing composition of claim 1, wherein the one or more acyl glycinate surfactants are selected from sodium cocoyl glycinate, sodium lauroyl glycinate, sodium myristoyl glycinate, potassium lauroyl glycinate, potassium cocoyl glycinate, or mixtures thereof.

3. The cleansing composition of claim 1, wherein the one or more acyl glycinate surfactants is sodium cocoyl glycinate.

4. The composition of claim 1, wherein the one or more magnesium salts are selected from magnesium chloride, magnesium sulfate, magnesium thiosulfate, magnesium pyrrolidone carboxylate (magnesium pidolate), magnesium gluconate, or mixtures thereof.

5. The composition of claim 1, wherein the one or more emulsifiers having an HLB of about 6 or less are selected from sorbitan esters, glyceryl esters, polyglyceryl esters, glycol esters, sucrose esters, methyl glucose esters, ethoxylated methyl glucose esters, or mixtures thereof.

6. The composition of claim 1, wherein at least one of the one or more nonionic emulsifiers having an HLB of about 6 or less are selected from glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinioleate, propylene glycol stearate, or mixtures thereof.

7. The composition of claim 1, wherein the one or more water soluble solvents are selected form glycerin, $C_2$-$C_6$ mono-alcohols, polyols, glycols, or mixtures thereof.

8. The composition of claim 7, wherein one of the one or more water soluble solvents is glycerin, in an amount from about 25 to about 50 wt. %, based on the total weight of the composition.

9. The composition of claim 1, wherein the one or more water soluble solvents of (d) and the water of (e) are in a weight ratio of about 0.5:1 to about 8:1 ((d):(e)).

10. The composition of claim 1, further comprising one or more salts providing monovalent cations.

11. The composition of claim 10, wherein the one or more salts are selected from sodium chloride, potassium chloride, sodium sulphate, potassium sulphate, ammonium chloride, monoethanolammonium chloride, or mixtures thereof.

12. The composition of claim 1, further comprising one or more skin active agents.

13. The composition of claim 1, wherein the composition is stable for at least 2 months in storage at 25° C., retaining at least 90% of its original volume, and maintaining a specific gravity of about 0.6 to about 0.8 g/mL.

14. A stable foamed cleansing composition comprising:
(a) about 8 wt. % to about 40 wt. % of one or more acyl glycinate surfactants selected from sodium cocoyl glycinate, sodium lauroyl glycinate, sodium myristoyl glycinate, potassium lauroyl glycinate, potassium cocoyl glycinate, or mixtures thereof;
(b) about 0.5 to about 2 wt. % of one or more magnesium salts selected from magnesium chloride, magnesium sulfate, magnesium thiosulfate, magnesium pyrrolidone carboxylate (magnesium pidolate), magnesium gluconate, or mixtures thereof;
(c) about 3 wt. % to about 7 wt. % of one or more nonionic emulsifiers having a Hydrophile-Lipophile Balance (HLB) of about 6 or less;
(d) about 30 to about 65 wt. % of one or more water soluble solvents selected form glycerin, polyols, glycols, or mixtures thereof; and
(e) about 10 to about 50 wt. % of water;
wherein (d) and (e) are in a weight ratio of about 1:1 to about 5:1;
(f) about 0.1 to about 3 wt. % of one or more one or more salts providing monovalent cations selected from sodium chloride, potassium chloride, sodium sulphate, potassium sulphate, ammonium chloride, monoethanolammonium chloride, or mixtures thereof;
(h) optionally, about 0.01 to about 6 wt. % of one or more miscellaneous ingredients;
wherein the composition has a lamellar liquid crystal structure,
the composition has been foamed by incorporation of an air or gas throughout the composition;
the composition has a specific gravity of about 0.6 to about 0.8 g/mL at 25° C., and
all percentages by weight are based on a total weight of unfoamed composition.

15. The composition of claim 14, wherein the one or more water soluble solvents are selected from ethylene glycol, propylene glycol, butylene glycol, hexylene glycol, pentylene glycol, diethylene glycol, dipropylene glycol, 1,3 propanediol, caprylyl glycol, glycerin, or mixtures thereof.

16. The composition of claim 15, wherein the one or more emulsifiers having an HLB of about 6 or less are selected from sorbitan esters, glyceryl esters, polyglyceryl esters, glycol esters, sucrose esters, methyl glucose esters, ethoxylated methyl glucose esters, or mixtures thereof.

17. The composition of claim 16, wherein the one or more acyl glycinate surfactants is sodium cocoyl glycinate.

18. The composition of claim 14, wherein the composition is stable for at least 2 months in storage at 25° C., retaining at least 90% of its original volume and maintaining a specific gravity of about 0.6 to about 0.8 g/mL.

19. A method for cleansing skin comprising applying the cleansing composition of claim 1 to the skin and rinsing the composition from the skin.

20. A cleansing product comprising the stable foamed cleansing composition of claim 1 within a container, wherein the product is not an aerosol and the product does not incorporate air or gas into the composition when dispensing the composition.

* * * * *